(12) United States Patent
Chakrabarti

(10) Patent No.: US 10,861,586 B2
(45) Date of Patent: Dec. 8, 2020

(54) SYSTEM AND METHODS FOR DETERMINATION OF TEMPERATURE CYCLING PROTOCOLS FOR POLYMERASE CHAIN REACTIONS

(71) Applicant: PMC ADVANCED TECHNOLOGY, LLC, Mt. Laurel, NJ (US)

(72) Inventor: Raj Chakrabarti, Moorestown, NJ (US)

(73) Assignee: CHAKRABARTI ADVANCED TECHNOLOGY, LLC, Mt. Laurel, NJ (US)

( * ) Notice: Subject to any disclaimer, the term of this patent is extended or adjusted under 35 U.S.C. 154(b) by 1140 days.

(21) Appl. No.: 14/892,924

(22) PCT Filed: May 22, 2014

(86) PCT No.: PCT/US2014/039251
§ 371 (c)(1),
(2) Date: Nov. 20, 2015

(87) PCT Pub. No.: WO2014/190215
PCT Pub. Date: Nov. 27, 2014

(65) Prior Publication Data
US 2016/0103952 A1    Apr. 14, 2016

Related U.S. Application Data

(60) Provisional application No. 61/826,269, filed on May 22, 2013, provisional application No. 61/982,108, filed on Apr. 21, 2014.

(51) Int. Cl.
*G16B 25/00* (2019.01)
*C12Q 1/6851* (2018.01)

(52) U.S. Cl.
CPC .......... *G16B 25/00* (2019.02); *C12Q 1/6851* (2013.01)

(58) Field of Classification Search
None
See application file for complete search history.

(56) References Cited

PUBLICATIONS

International Search Report and Written Opinion for corresponding PCT application PCT/US2014/039251, dated Dec. 5, 2014, 13 pages.
Mamedov, T.G. et al., A Fundamental Study of the PCR Amplification of GC-Rich DNA Templates, Computational Biology and Chemistry, Elsevier, Amsterdam, NL, vol. 32, No. 6, Dec. 1, 2008, pp. 452-457.
Anonymous: Nucleic Acid Thermodynamics, Wikipedia, the free encyclopedia, Apr. 26, 2013, XP055154424, retrieved from internet, 8 pages.
Anonymous: Chemical Kinetics, Mar. 27, 2001, XP055154620, retrieved from internet, 10 pages.
Vallance, Dr. Claire et al., Reaction Kinetics, Mar. 7, 2008, pp. 1-31, XP055154613.
Vallone, Peter M. et al., Predicting Sequence-Dependent Melting Stability of Short Duplex DNA Oligomers, Biopoly, Jan. 1, 1998, pp. 217-239, XP055155018, retrieved from internet.
Velikanov, Mikhail V. et al., Polymerase Chain Reaction: A Markov Process Approach, Journal of Theoretical Biology, vol. 201, No. 4, Dec. 1, 1999, pp. 239-249.

*Primary Examiner* — Joseph Woitach
(74) *Attorney, Agent, or Firm* — J. Clinton Wimbish; Nexsen Pruet, PLLC

(57) ABSTRACT

In one aspect, methods are described herein for enhancing one or more nucleic acid interactions. For example, in some embodiments, methods of enhancing one or more steps of polymerase chain reaction (PCR) are described herein. In some embodiments, the optimal temperature cycling protocol for one or more PCR cycles can be determined according to methods described herein.

35 Claims, 23 Drawing Sheets
Specification includes a Sequence Listing.

Reaction scheme for polymerase-mediated DNA extension.

Flowchart for calculation of polymerase extension rate constants.

$$g_1(x) = [x_{15} \; 0 \; 0 \; 0 \; 0 \; 0 \; 0 \; x_{15} \; 0 \; 0 \; 0 \; 0 \; 0 \; -x_{15} \; 0 \; 0]^T \Big\} \text{sequence-dependent melting}$$

$$g_2(x) = [-x_1 x_8 \; 0 \; 0 \; 0 \; 0 \; 0 \; 0 \; -x_1 x_8 \; 0 \; 0 \; 0 \; 0 \; 0 \; x_1 x_8 \; 0 \; 0]^T$$

$$g_3(x) = [-x_1 x_2 \; - \; x_1 x_2 \; x_1 x_2 \; 0 \; 0 \; 0 \; 0 \; 0 \; 0 \; 0 \; 0 \; 0 \; 0 \; 0 \; 0 \; 0]^T \Big\} \text{sequence-dependent annealing}$$

$$g_4(x) = [x_3 \; x_3 \; - \; x_3 \; 0 \; 0 \; 0 \; 0 \; 0 \; 0 \; 0 \; 0 \; 0 \; 0 \; 0 \; 0 \; 0]^T$$

$$g_5(x) = [0 \; 0 \; 0 \; 0 \; 0 \; 0 \; 0 \; - \; x_8 x_9 \; - \; x_8 x_9 \; x_8 x_9 \; 0 \; 0 \; 0 \; 0 \; 0 \; 0]^T$$

$$g_6(x) = [0 \; 0 \; 0 \; 0 \; 0 \; 0 \; 0 \; 0 \; x_{10} \; - \; x_{10} \; 0 \; 0 \; 0 \; 0 \; 0 \; 0]^T$$

$$g_7(x) = x_{17}[0 \; 0 \; - \; x_3 \; x_3 \; - \; x_5 \; x_5 \; 0 \; 0 \; 0 \; 0 \; - \; x_{10} \; x_{10} \; - \; x_{12} \; x_{12} \; 0 \; 0 \; - \; (x_3 + x_5 + x_{10} + x_{12})]^T$$

$$g_8(x) = [0 \; 0 \; x_4 \; - \; x_4 \; x_6 \; - \; x_6 \; 0 \; 0 \; 0 \; 0 \; x_{11} \; - \; x_{11} \; x_{13} \; - \; x_{13} \; 0 \; 0 \; (x_4 + x_6 + x_{11} + x_{13}) \; 0]^T \Big\} \text{sequence-dependent enzyme binding}$$

$$g_9(x) = x_{16}[0 \; 0 \; 0 \; - \; x_4 \; 0 \; 0 \; - \; x_6 \; x_6 \; 0 \; 0 \; 0 \; - \; x_{11} \; x_{11} \; - \; x_{13} \; x_{13} \; 0 \; (x_4 + x_6 + x_{11} + x_{13}) \; 0]^T$$

$$g_{10}(x) = [0 \; 0 \; 0 \; 0 \; 0 \; 0 \; - \; x_7 \; 0 \; 0 \; 0 \; 0 \; 0 \; 0 \; - \; x_{14} \; 0 \; 0 \; x_7 + x_{14}]^T \Big\} \text{extension}$$

FIG. 18

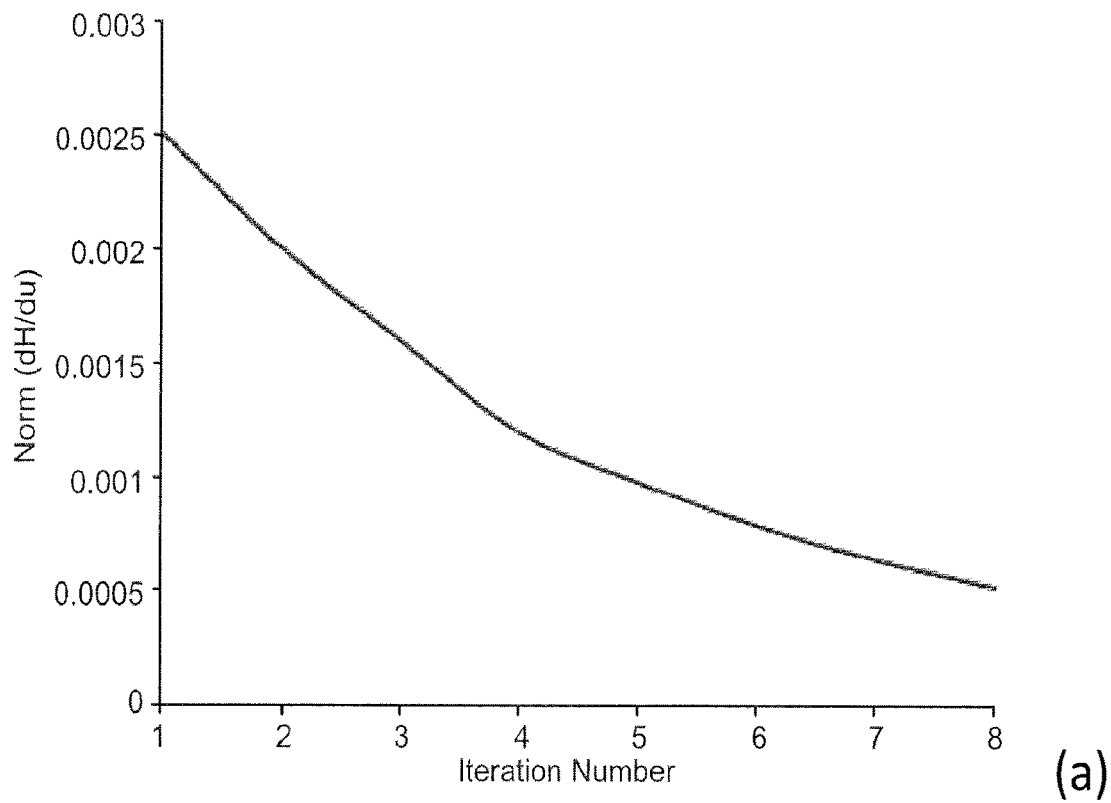
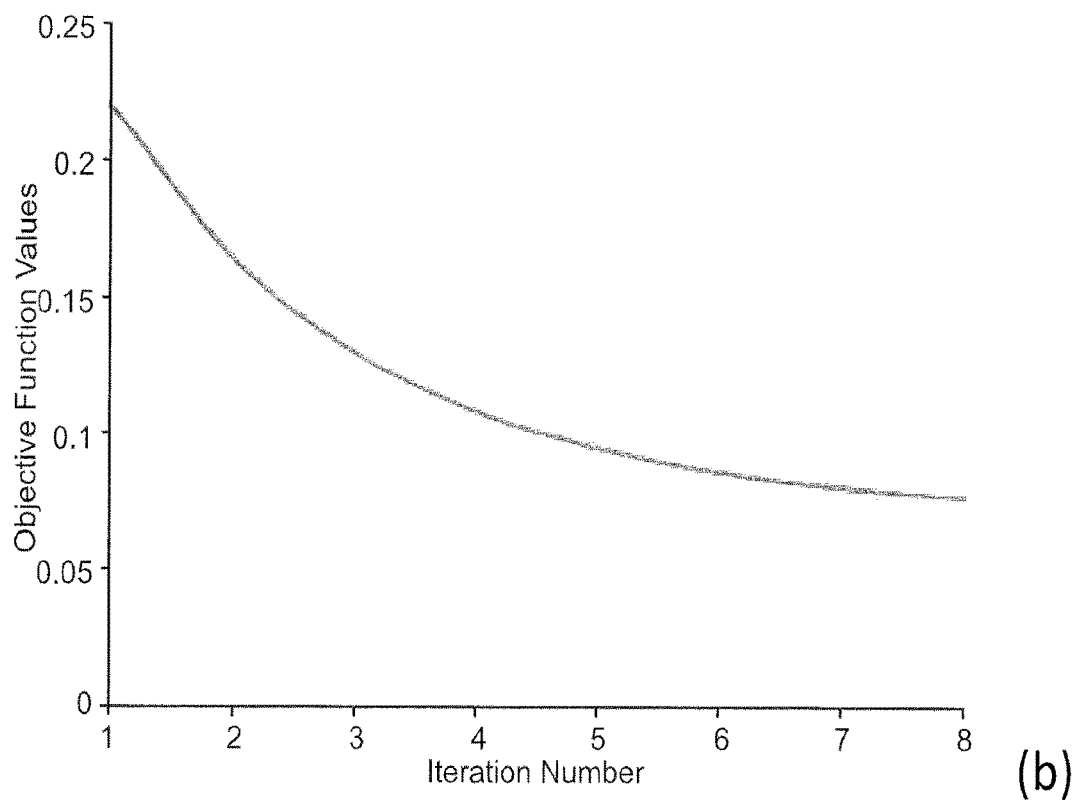
FIG. 22

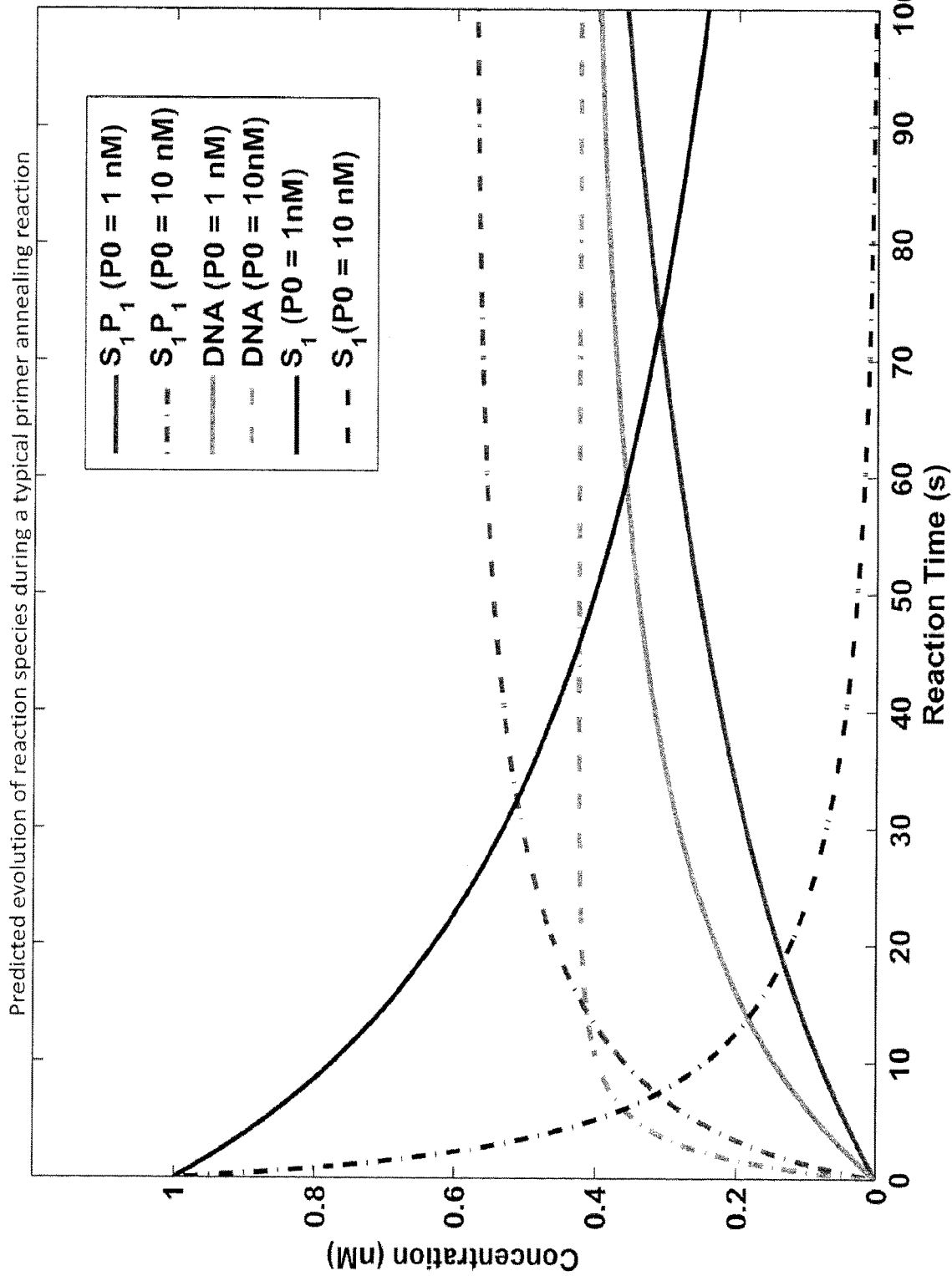

SYSTEM AND METHODS FOR DETERMINATION OF TEMPERATURE CYCLING PROTOCOLS FOR POLYMERASE CHAIN REACTIONS

RELATED APPLICATION DATA

The present application hereby claims priority pursuant to 35 U.S.C. § 119(e) to U.S. Provisional Patent Application Ser. No. 61/826,269 filed May 22, 2013 and U.S. Provisional Patent Application Ser. No. 61/982,108 filed Apr. 21, 2014, each of which is incorporated by reference in its entirety.

BACKGROUND

The polymerase chain reaction (PCR), the most common DNA amplification reaction, is a cyclic amplification process that can produce millions of copies of double-stranded DNA molecules starting from a single molecule. The traditional PCR reaction cycle consists of three temperature steps that induce (i) double-stranded DNA denaturation, (ii) oligonucleotide primer annealing to the resulting single-stranded DNAs, and (iii) polymerase enzyme-mediated extension to produce two double-stranded DNA molecules. This cycle is repeated 20-30 times, resulting in geometric growth of the number of DNA molecules. Despite the apparent simplicity of the PCR reaction, standard PCR temperature cycling approaches are often fraught with difficulties that can decrease the average cycle efficiency or result in competitive amplification of undesired side products. Due to geometric amplification, this can result in dramatically diminished efficiency and specificity of the overall reaction.

SUMMARY

In one aspect, methods are described herein for enhancing one or more nucleic acid interactions. For example, in some embodiments, methods of enhancing one or more steps of polymerase chain reaction (PCR) are described herein. In some embodiments, the optimal temperature cycling protocol for one or more PCR cycles can be determined according to methods described herein. In some embodiments, a computer implemented method for enhancing annealing efficiency of first and second single strands of deoxyribonucleic acid (DNA) over a predetermined time period is described herein, the method comprising accessing a memory via a computing device processor, wherein the memory comprises computer instructions that when operated by the computing device processor cause the computing device processor to receive information comprising sequences of the first and second DNA strands, concentrations of the first and second DNA strands, length of the predetermined time period and a set of annealing reaction temperatures; determine the forward reaction rate constant, $k_f$, of annealing the first and second single strands of DNA at annealing reaction temperatures in the set; determine the reverse reaction rate reaction rate constant, $k_r$, of annealing the first and second single strands of DNA at annealing reaction temperatures in the set; and select one or more of the annealing reaction temperatures sufficient to produce a DNA concentration from the annealed first and second strands in excess of a predetermined threshold within the predetermined time period.

In another embodiment, a computer implemented method for enhancing annealing efficiency of first and second single strands of deoxyribonucleic acid (DNA) at a predetermined temperature is described herein, the method comprising accessing a memory via a computing device processor, where the memory comprises computer instructions that when operated by the computing device processor causes the computing device processor to receive information comprising sequences of the first and second DNA strands, concentrations of the first and second DNA strands, the predetermined annealing reaction temperature and a set of annealing reaction time periods; determine the forward reaction rate constant, $k_f$, of annealing the first and second single strands of DNA; determine the reverse reaction rate reaction rate constant, $k_r$, of annealing the first and second single strands of DNA; and select one or more of the annealing reaction time periods sufficient to produce a DNA concentration from the annealed first and second strands in excess of a predetermined threshold at the predetermined annealing reaction temperature.

In another aspect, a computer implemented method for enhancing amplification efficiency of a sequence of deoxyribonucleic acid (DNA) in a first cycle of polymerase chain reaction (PCR) is described herein, the method comprising accessing a memory via a computing device processor, where the memory comprises computer instructions that when operated by the computing device processor causes the computing device processor to (a) receive information comprising sequences of single strand DNA and primer, concentrations of the single strand DNA and primer, length of a predetermined time period for annealing the single strand DNA and primer and a set of annealing reaction temperatures; (b) determine the forward reaction rate constant, $k_f$, of annealing the single strand DNA and primer at annealing reaction temperatures in the set; (c) determine the reverse reaction rate reaction rate constant, $k_r$, of annealing the single strand DNA and primer at reaction temperatures in the set; and (d) select one or more of the annealing reaction temperatures sufficient to produce a primer hybridized DNA strand concentration in excess of a predetermined threshold within the predetermined time period for annealing.

In some embodiments, the computing device further (a') determines a time period for duplex DNA melting sufficient to produce a concentration of single strand DNA in excess of a predetermined threshold. Determining the time period for duplex DNA melting can comprise determining forward and reverse rate constants of duplex DNA melting by at least one of:

(1) identification of different melting domains for a given DNA sequence using an algorithmic method;

(2) ascending ordering of domains based on melting temperature, wherein the equilibrium constant of each domain as a function of temperature is calculated via the equation:

$$K_{eq,dom} = \sigma_c f(N) \prod_{i=1}^{N} s_i$$

where N is the domain length, $s_i$ is the equilibrium constant for formation of base pair i and $\sigma_c$ is the cooperativity parameter that constitutes a penalty on the statistical weight $$\prod_{i=1}^{N} s_i$$

for melting of the domain due to the free energy cost of dissociation of an internal base pair, and f(N) is a loop closure function specific to the type of domain that introduces a length dependence on the free energy cost;

(3) construction of state space matrices based on a two-sided or one sided matrix for each domain;

(4) association of σ, the nucleation parameter with individual states in a last block as in the matrix below;

(5) diagonalization of each block and rank ordering of eigenvalues of all blocks;

(6) determining relaxation time, τ, according to 1/max$(\lambda_i)$, wherein max$(\lambda_i)$ denotes the largest eigenvalue of an annealing reaction matrix of the form (here depicted for a two base sequence)

$$A = \begin{bmatrix} -(k^{-1}+k_{-1}) & k_1 & k_1 & 0 \\ k_{-1} & -(k_{-2}+k_1) & 0 & \sigma[D_{0,2eq}]k_1 \\ k^{-1} & 0 & -(k^{-2}+k_1) & \sigma[D_{0,2eq}]k_1 \\ 0 & k_{-2} & k^{-2} & -2\sigma[D_{0,2eq}]k_1 \end{bmatrix}$$

wherein $k_0=k_1=k_2$ which equal the forward rate constant for formation of a single base pair and $k_{-i}$ is the reverse rate constant for the formation of the single base pair wherein $k_{-i}=s_i/k_0$ where s is the equilibrium constant for formation of base pair i, and σ is a nucleation parameter that measures resistance to formation of the first base pair.

(7) comparing all relaxation times and identifying the maximum value of the relaxation time as the relaxation time of the whole DNA sequence (8) computing forward and reverse rate constants $k_m, k_{-m}$ for DNA melting based on the relaxation time and the Gibbs free energy of melting.

Additionally, in some embodiments, the computing device processor further (e) determines a time period for DNA extension sufficient to produce a concentration of DNA in excess of a predetermined threshold. Determining the time period for DNA extension can comprise determining the forward reaction rate constant, $k_e$, of DNA polymerase binding and determining the reverse reaction rate constant, $k_{-e}$ of DNA polymerase binding. $k_e$ and $k_{-e}$ can be determined according to the processivity of the polymerase and the Gibbs free energy for the DNA polymerase binding reaction through the relationships $$K_{binding} = \frac{k_e}{k_{-e}}$$

and:

$$k_{-e} = \frac{k_{cat}}{K_N}[N]\left(\frac{1}{E[i_{off}]-1}\right)$$

where i indexes the sequence position on the template, $$\frac{K_{cat}}{K_N}$$

is the apparent second order rate constant of nucleotide addition, and $$E[i_{off}] = \frac{1}{1-p}$$

is the processivity or expected position of dissociation of the polymerase, with p denoting the microscopic processivity parameter, the microscopic processivity parameter being the conditional probability of the polymerase not dissociating at position/time i, given that it was bound to the template at position i−1. Additionally, determining the time period for DNA extension can further comprise determining the enzyme bound hybridized DNA strand concentration, [E.SP] and the concentrations of all enzyme bound partially extended DNA molecules according to:

$$\frac{d}{dt}[E.SP] = k_e[E][SP] - k_{-e}[E.SP] - \frac{k_{cat}}{K_N}[N][E.SP]$$

$$\frac{d}{dt}[E.D_i] = k_e[E][D_i] - k_{-e}[E.D_i] + \frac{k_{cat}}{K_N}[N]\{[E.D_{i-1}] - [E.D_i]\},$$

$$i = 1, \ldots, n-1$$

where [N] is the nucleotide concentration, $[E.D_i]$ is the concentration of enzyme bound primer-template DNA with i added nucleotides, and n denotes the number of bases in the DNA sequence. $K_N$ and $k_{cat}$ can be theoretically determined or determined from a plot of 1/v versus 1/[N] wherein the slope of the plot is approximately $$\frac{K_N}{K_{cat}E_0}$$

and the y-intercept is $$\frac{1}{k_{cat}E_0},$$

wherein $E_0$ is the initial concentration of DNA polymerase and v is an experimentally or theoretically determined rate of reaction for nucleotide addition.

Amplification of the DNA concentration in excess of a predetermined threshold can be achieved through an algorithm that solves an optimization problem of the form $$\min_{T(t)} J, J = \sum_{i=1}^{4n+4} x_i(t_f)$$

subject to the constraint $$\frac{dx}{dt} = f(x(t), T(t), k), x(0) = x_0$$

where T(t) denotes the temperature of the reaction mixture as a function of reaction time, $x=[[S_1], [S_1P_1], [E.S_1P_1], [D_1^1], [E.D_1^1], \ldots, [DNA], [P_1], [P_2], [N], [E]]^{Tr}$ is the vector of concentrations of all reaction species, $x_0$ denotes the vector of initial concentrations, $t_f$ denotes the predetermined time for a single PCR cycle, and f(x(t), T(t), k) denotes the right-hand side of the system of rate equations for primer annealing, enzyme binding and polymerase-mediated extension and k is a vector of all kinetic rate constants appearing in the system of PCR rate equations. f(x(t), T(t), k) can be expressed in terms of the sequence-dependent rate constants $k_i$ appearing in $$\left[k_m, k_{-m}, k_f^1, k_r^1, k_f^2, k_r^2, k_1^e, k_{-1}^e, \frac{k_{cat}}{K_N}, k'_{cat}\right] \text{ as } \sum_i k_i(T(t))g_i(x(t))$$

$g_i(x(t))$ denotes the part of the right-hand side of the system of rate equations for DNA melting, primer annealing, enzyme binding and polymerase-mediated extension associated with rate constant $k_i$. Additionally, the optimization problem, in such embodiments, can be formulated as a system of differential-algebraic equations (DAE) of:

$$H[x(t), \phi(t), T(t)] = \phi^{Tr}(t) \sum_{i=1}^{10} k_i(T(t))g_i(x(t))$$

$$\frac{d\phi}{dt} = -\nabla_x H[x(t), \phi(t), T(t)] = -\sum_{i=1}^{10} k_i(T(t))\left(\frac{\partial g_i(x(t))}{\partial x(t)}\right)^{Tr}\phi(t)$$

$$\phi(t_f) = [\nabla_x F(x(t))]_{t=t_f} = \left[\nabla_x \sum_{i=1}^{4n+4} x_i(t)\right]_{t=t_f}$$

$$\frac{\partial H}{\partial T(t)}[x^*(t), \phi^*(t), T^*(t)] = \phi^{*,Tr}(t) \sum_{i=1}^{10} \frac{\partial k_i(T(t))}{\partial T(t)}\bigg|_{T^*(t)} g_i(x^*(t)) = 0,$$

$$\forall t \in [0, t_f]$$

where H denotes the optimal control Hamiltonian function and $\phi(t)$ denotes the optimal control costate vector.

Alternatively, the optimal control problem, in some embodiments, is of the form:

$$\min_{T(t)} J, J = t_f$$

subject to the constraints $$\frac{dx}{dt} = f(x(t), T(t), k), x(0) = x_0 \quad \text{i)}$$

$$[DNA](t_f) = [DNA]_{target} \quad \text{ii)}$$

where T(t) denotes the temperature of the reaction mixture as a function of reaction time, is the vector of concentrations of all reaction species, $t_f$ denotes the predetermined time for a single PCR cycle, and f(x(t), T(t), k) denotes the right-hand side of the system of rate equations for primer annealing, enzyme binding and polymerase-mediated extension and k is a vector of all kinetic rate constants appearing in the system of rate equations. As described above, f(x(t), T(t), k) can be expressed in terms of the sequence-dependent rate constants $k_i$ appearing in $$\left[k_m, k_{-m}, k_f^1, k_r^1, k_f^2, k_r^2, k_e, k_{-e}, \frac{k_{cat}}{K_N}, k'_{cat}\right] \text{ as } \sum_i k_i(T(t))g_i(x(t)).$$

In such embodiments, the optimization problem can be formulated as a system of differential-algebraic equations (DAE) of:

$$H[x(t), T(t), \phi(t)] =$$

$$L[x(t), T(t)] + \phi^{Tr}(t)\sum_{i=1}^{10} k_i(T(t))g_i(x(t)) = 1 + \phi^{Tr}(t)\sum_{i=1}^{10} k_i(T(t))g_i(x(t))$$

$$\frac{d\phi}{dt} = -\nabla_x H = -\sum_{i=1}^{10} k_i(T(t))\left(\frac{\partial g_i(x(t))}{\partial x(t)}\right)^{Tr}\phi(t)$$

$$\frac{\partial H}{\partial T(t)}[x^*(t), \phi^*(t), T^*(t)] = \phi^{*,Tr}(t) \sum_{i=1}^{10} \frac{\partial k_i(T(t))}{\partial T(t)}\bigg|_{T^*(t)} g_i(x^*(t)) = 0,$$

$$\forall t \in [0, t_f]$$

$$\phi_i(t_f) = 0, i = 1, \ldots, 4n+4$$

$$x_{4n+5}(t_f) = x_{4n+5,f}, x_{4n+5,f} > 2^m x_{4n+5}(0).$$

$$H|_{t_f} = 0 \Rightarrow \phi^{Tr}(t_f) \sum_{i=1}^{10} k_i(T(t_f))g_i(x(t_f)) = -1.$$

where H denotes the optimal control Hamiltonian function, $\phi(t)$ denotes the optimal control costate vector, and * denotes the solution to the optimal control problem.

Moreover, the instructions can cause the computing device processor to repeat steps (a)-(e) for enhancing amplification efficiency of the sequence of DNA in at least one additional cycle of PCR.

In another aspect, a computer implemented method is described herein for determining the temperature cycling protocol for a PCR reaction that achieves amplification of DNA concentration in excess of a predetermined threshold, the method comprising:

accessing a memory via a computing device processor, where the memory comprises computer instructions that when operated by the computing device processor causes the computing device processor to:
  a) receive information comprising sequences of single strand DNAs and primers, concentrations of the single strand DNAs and primers, the type of polymerase enzyme, the polymerase enzyme concentration, and the nucleotide concentration;
  b) determine the forward reaction rate constant, $k_f(T)$, of annealing each single strand DNA and primer as a function of temperature T;
  c) determine the reverse reaction rate constant, kr(T), of annealing each single strand DNA and primer as a function of temperature T;
  d) determine the rate constant, $k_e(T)$, of polymerase enzyme binding to the hybridized primer-template DNA as a function of temperature T;
  e) determine the rate constant, $k_{-e}(T)$, polymerase enzyme dissociation from the hybridized primer-template DNA as a function of temperature T
  f) determine the Michaelis constant, $K_N(T)$, for nucleotide binding to the enzyme-primer-template DNA complex E.SP as a function of temperature T
  g) determine the catalytic rate constant, $k_{cat}(T)$, of nucleotide addition to the enzyme-primer-template DNA complex E.SP as a function of temperature T
  h) determine the forward rate constant, $k_m(T)$, for dsDNA melting for the complete sequence as a function of temperature T
  i) determine the reverse rate constant, $k_{-m}(T)$, for dsDNA melting for the complete sequence as a function of temperature T solve an optimization problem of the form $$\min_{T(t)} J, J = \sum_{i=1}^{4n+4} x_i(t_f)$$

subject to the constraint $$\frac{dx}{dt} = f(x(t), T(t), k), x(0) = x_0$$

where T(t) denotes the temperature of the reaction mixture as a function of reaction time, $x=[[S_1], [S_1P_1], [E.S_1P_1], [D_1^1], [E.D_1^1], \ldots, [DNA], [P_1], [P_2], [N], [E]]^{Tr}$ is the vector of concentrations of all reaction species, $x_0$ denotes the vector of initial concentrations, $t_f$ denotes the predetermined time for a single PCR cycle, and f(x(t), T(t), k) denotes the right-hand side of the system of rate equations for primer annealing, enzyme binding and polymerase-mediated extension and k is a vector of all kinetic rate constants appearing in the system of PCR rate equations. f(x(t), T(t), k) can be expressed in terms of the sequence-dependent rate constants $k_i$ appearing in $$\left[k_m, k_{-m}, k_f^1, k_r^1, k_f^2, k_r^2, k_e, k_{-e}, \frac{k_{cat}}{K_N}, k'_{cal}\right] \text{ as } \sum_i k_i(T(t))g_i(x(t))$$

$g_i(x(t))$ denotes the part of the right-hand side of the system of rate equations for DNA melting, primer annealing, enzyme binding and polymerase-mediated extension associated with rate constant $k_i$. Alternatively, the solved optimization problem can be in the form:

$$\min_{T(t)} J, J = t_f$$

subject to the constraints $$\frac{dx}{dt} = f(x(t), T(t), k), x(0) = x_0 \quad \text{ii)}$$

$$[DNA](t_f) = [DNA]_{target} \quad \text{ii)}$$

where T(t) denotes the temperature of the reaction mixture as a function of reaction time, is the vector of concentrations of all reaction species, $t_f$ denotes the predetermined time for a single PCR cycle, and f(x(t), T(t), k) denotes the right-hand side of the system of rate equations for primer annealing, enzyme binding and polymerase-mediated extension and k is a vector of all kinetic rate constants appearing in the system of rate equations. As described above, f(x(t), T(t), k) can be expressed in terms of the sequence-dependent rate constants $k_i$ appearing in $$\left[k_m, k_{-m}, k_f^1, k_r^1, k_f^2, k_r^2, k_e, k_{-1}^e, \frac{k_{cat}}{K_N}, k'_{cal}\right] \text{ as } \sum_i k_i(T(t))g_i(x(t)).$$

In another aspect, a computer-readable medium storing computer-executable instructions is described herein that, when executed, cause a processor of a computing device to perform a method comprising receiving information comprising sequences of first and second single strands of DNA, concentrations of the first and second single strands of DNA, a predetermined reaction time period for annealing the first and second single strands of DNA and a set of annealing reaction temperatures; determining the forward reaction rate constant, $k_f$, of annealing the first and second single strands of DNA at annealing reaction temperatures in the set; determining the reverse reaction rate reaction rate constant, $k_r$, of annealing the first and second single strands of DNA at reaction temperatures in the set; and selecting one or more of the annealing reaction temperatures sufficient to produce a DNA concentration from the annealed first and second strands in excess of a predetermined threshold within the predetermined time period.

In another aspect, a system for enhancing annealing efficiency of first and second single strands of deoxyribonucleic acid (DNA) over a predetermined time period is described herein, the system comprising a memory device; and a processor coupled to the memory device, the processor configured to receive information comprising sequences of first and second single strands of DNA, concentrations of the first and second single strands of DNA, a predetermined time period for annealing the first and second single strands of DNA and a set of annealing reaction temperatures; determine the forward reaction rate constant, $k_f$, of annealing the first and second single strands of DNA at annealing reaction temperatures in the set; determine the reverse reaction rate reaction rate constant, $k_r$, of annealing the first and second single strands of DNA at annealing reaction temperatures in the set; and select one or more of the annealing reaction temperatures sufficient to produce a DNA concentration from the annealed first and second strands in excess of a predetermined threshold within the predetermined time period.

In a further aspect, a system for enhancing amplification efficiency of a sequence of DNA in a first cycle of PCR is described herein, the system comprising a memory device and a processor coupled to the memory device, the processor configured to (a) receive information comprising sequences of single strand DNA and primer, concentrations of the single strand DNA and primer, length of a predetermined time period for annealing the single strand DNA and primer and a set of annealing reaction temperatures; (b) determine the forward reaction rate constant, $k_f$, of annealing the single strand DNA and primer at annealing reaction temperatures in the set; (c) determine the reverse reaction rate reaction rate constant, $k_r$, of annealing the single strand DNA and primer at reaction temperatures in the set; and (d) select one or more of the annealing reaction temperatures sufficient to produce a primer hybridized DNA strand concentration in excess of a predetermined threshold within the predetermined time period for annealing. In some embodiments, the processor is further configured to (e) determine a time period for DNA extension sufficient to produce a concentration of DNA in excess of a predetermined threshold as described herein.

These and other aspects are further described in the detailed description which follows.

according to some embodiments described herein.

Figure 11:
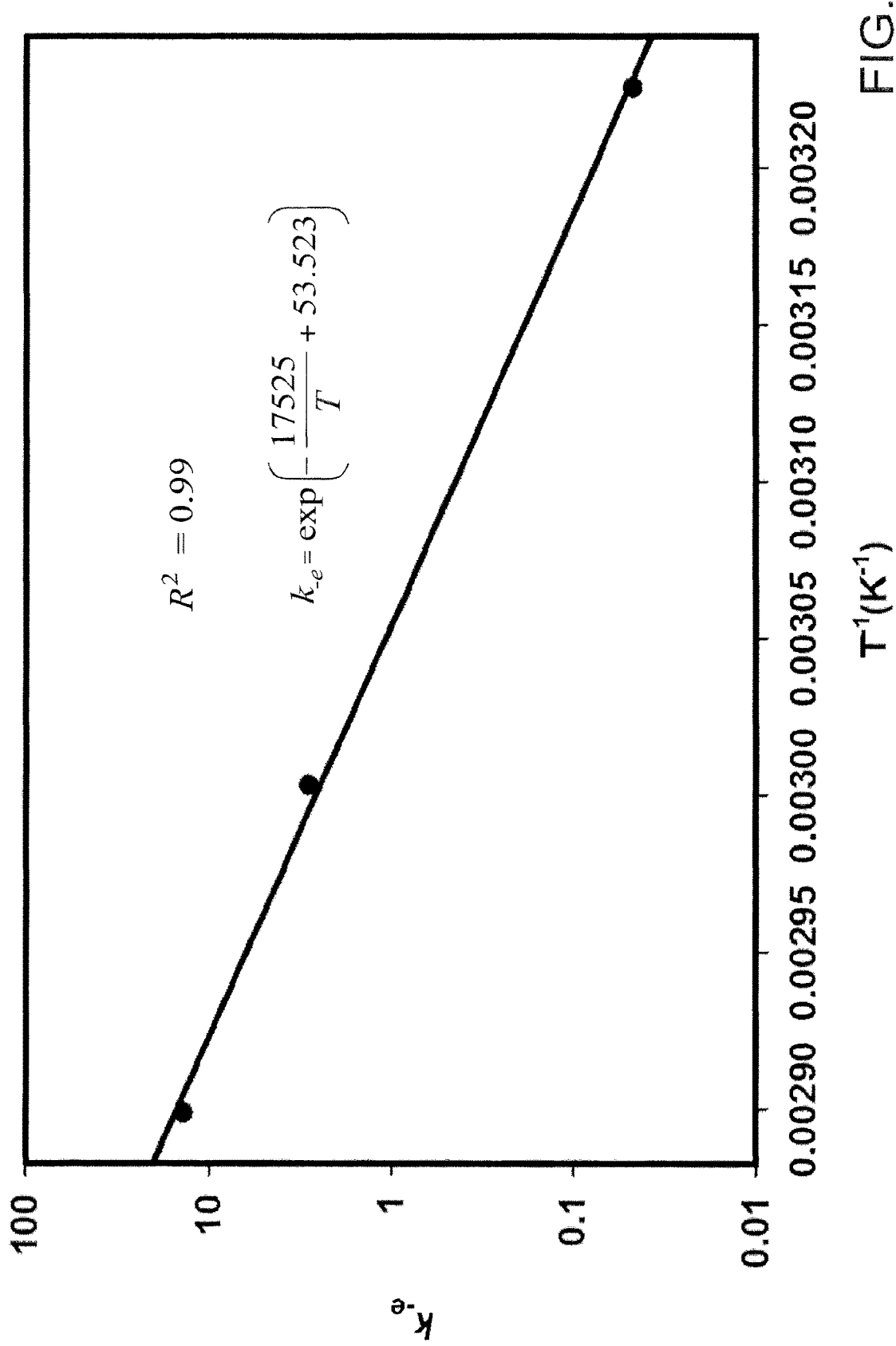

FIG. 11 illustrates $k_{-e}$ of DNA extension at three different temperatures according to some embodiments described herein.

Figure 12:
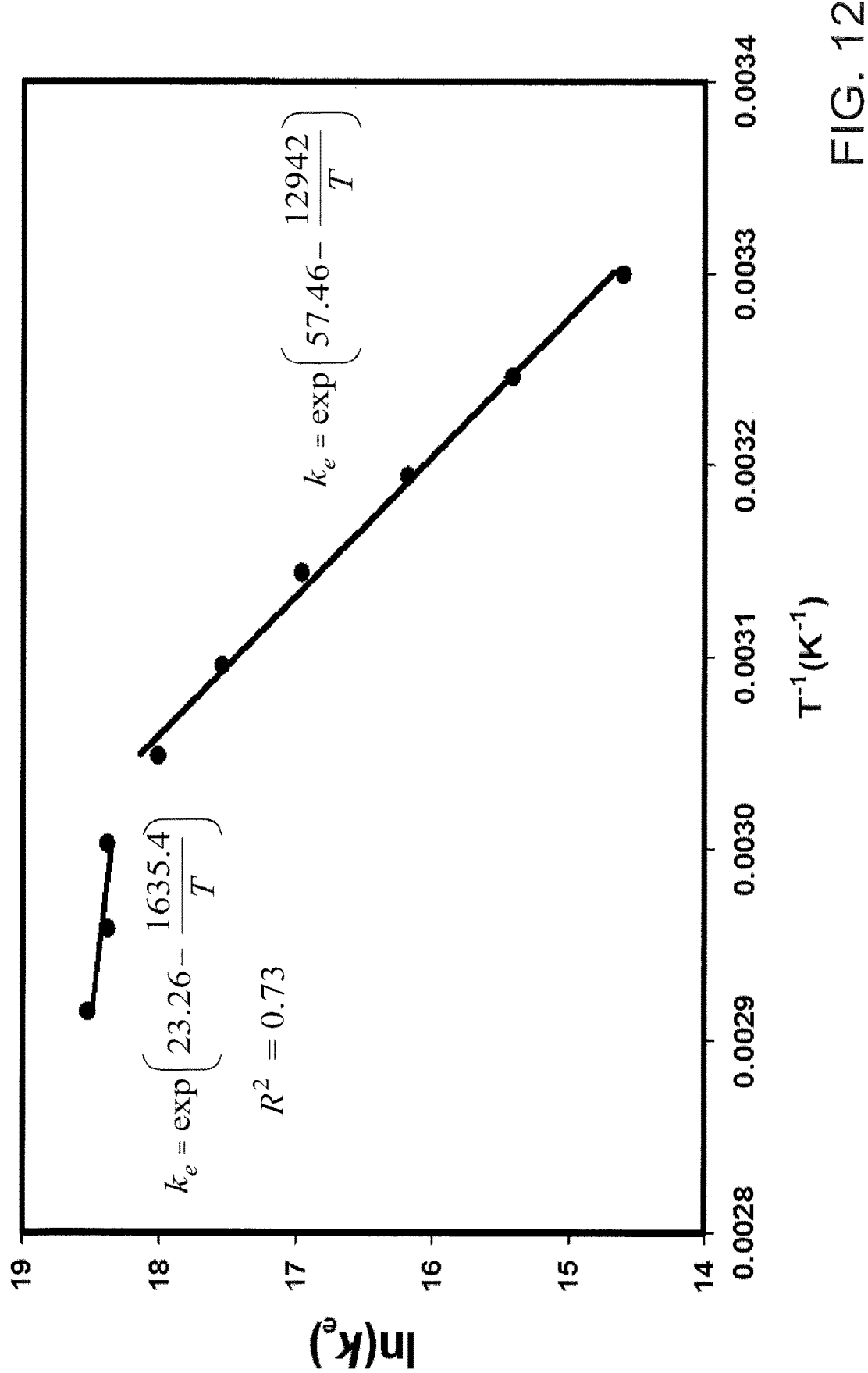

FIG. 12 provides estimates of $k_1$ based on temperature dependence of $k_{-1}$ as illustrated in the Arrhenius plot.

Figure 13:
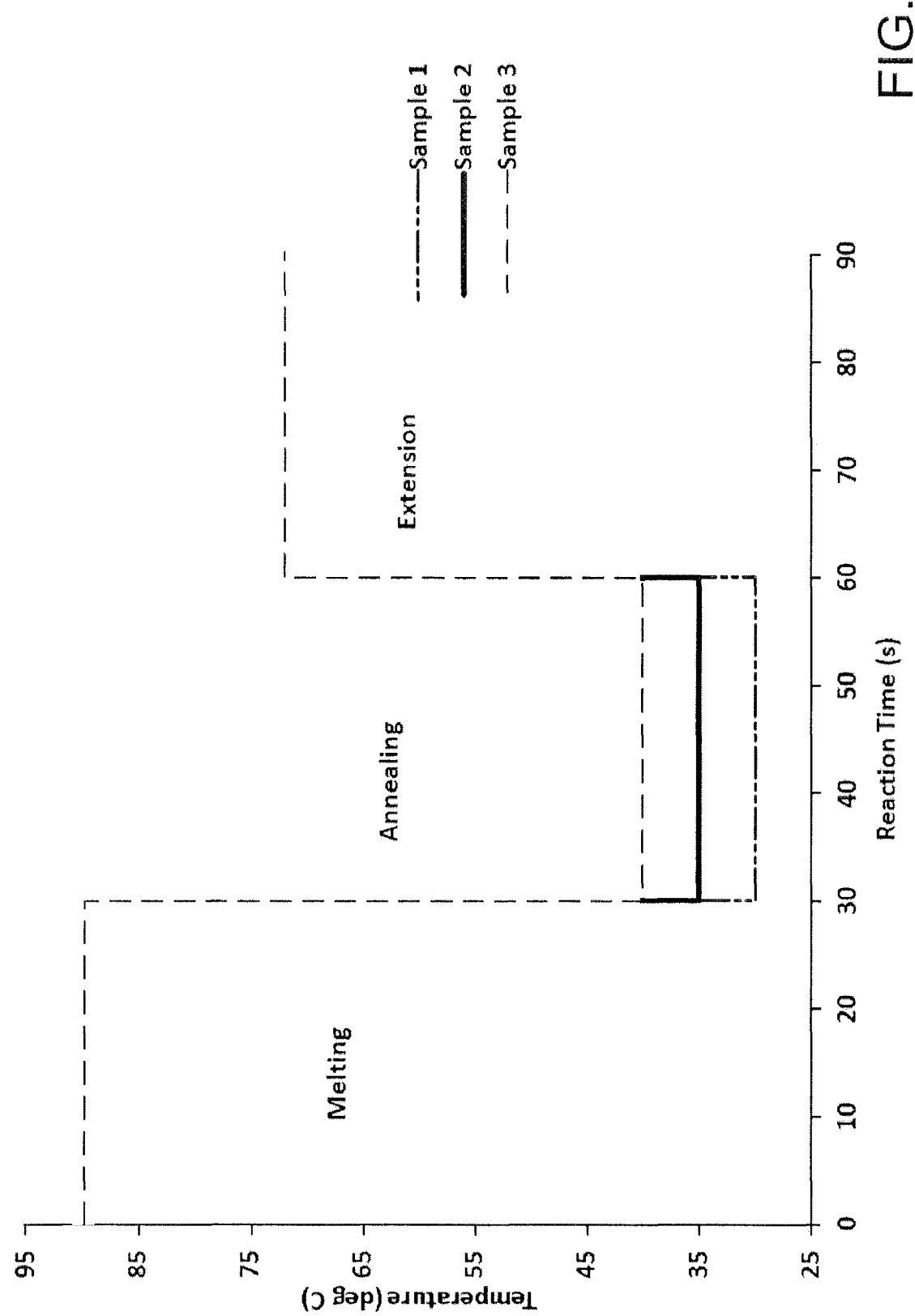

FIG. 13 provides temperatures and reaction times for melting, annealing and extension steps of a first cycle of PCR according to one embodiment described herein.

Figure 14:
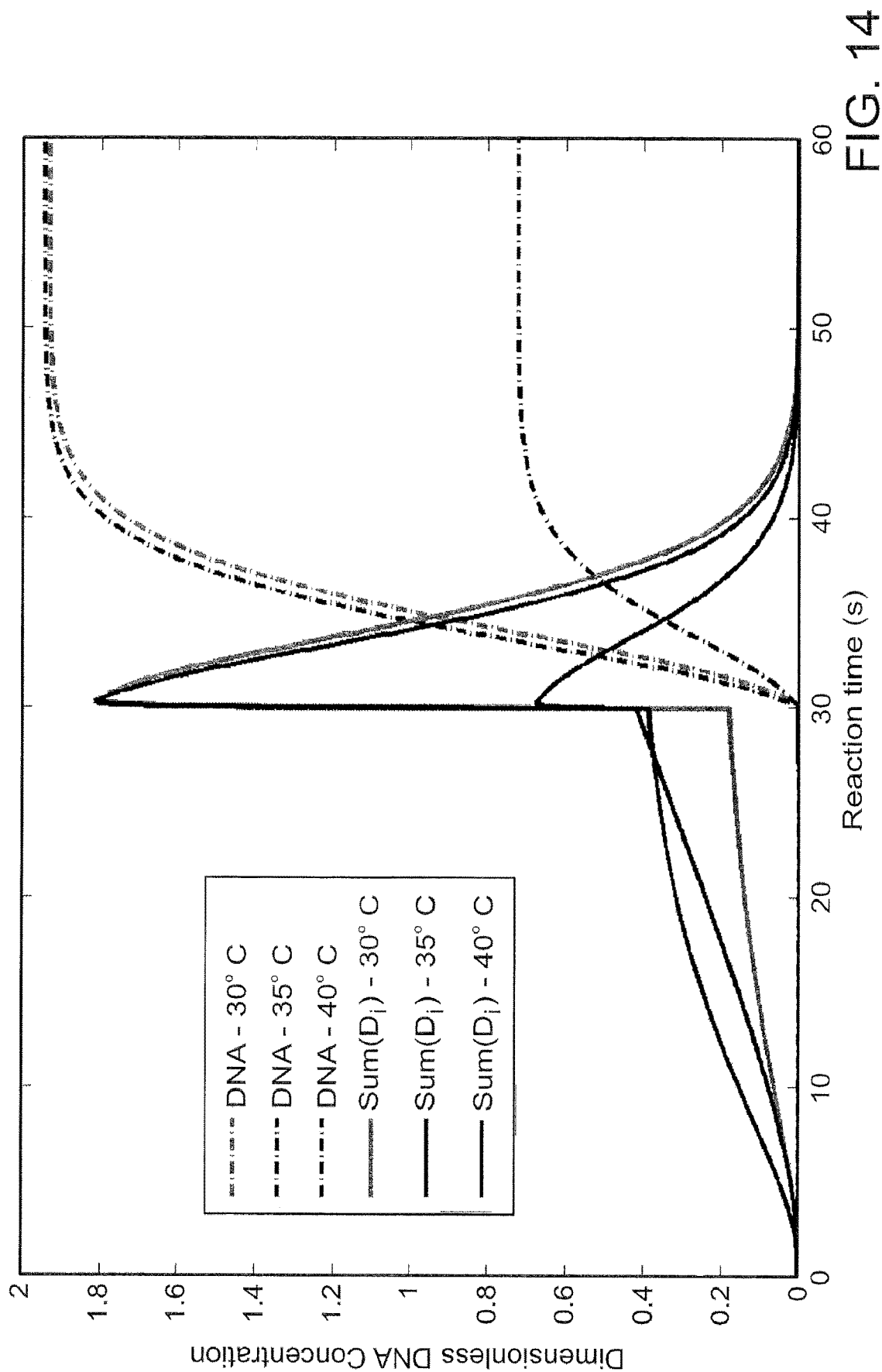

FIG. 14 illustrates solutions to the system of rate equations for the entire PCR cycle for the three different annealing temperatures.

Figure 15:
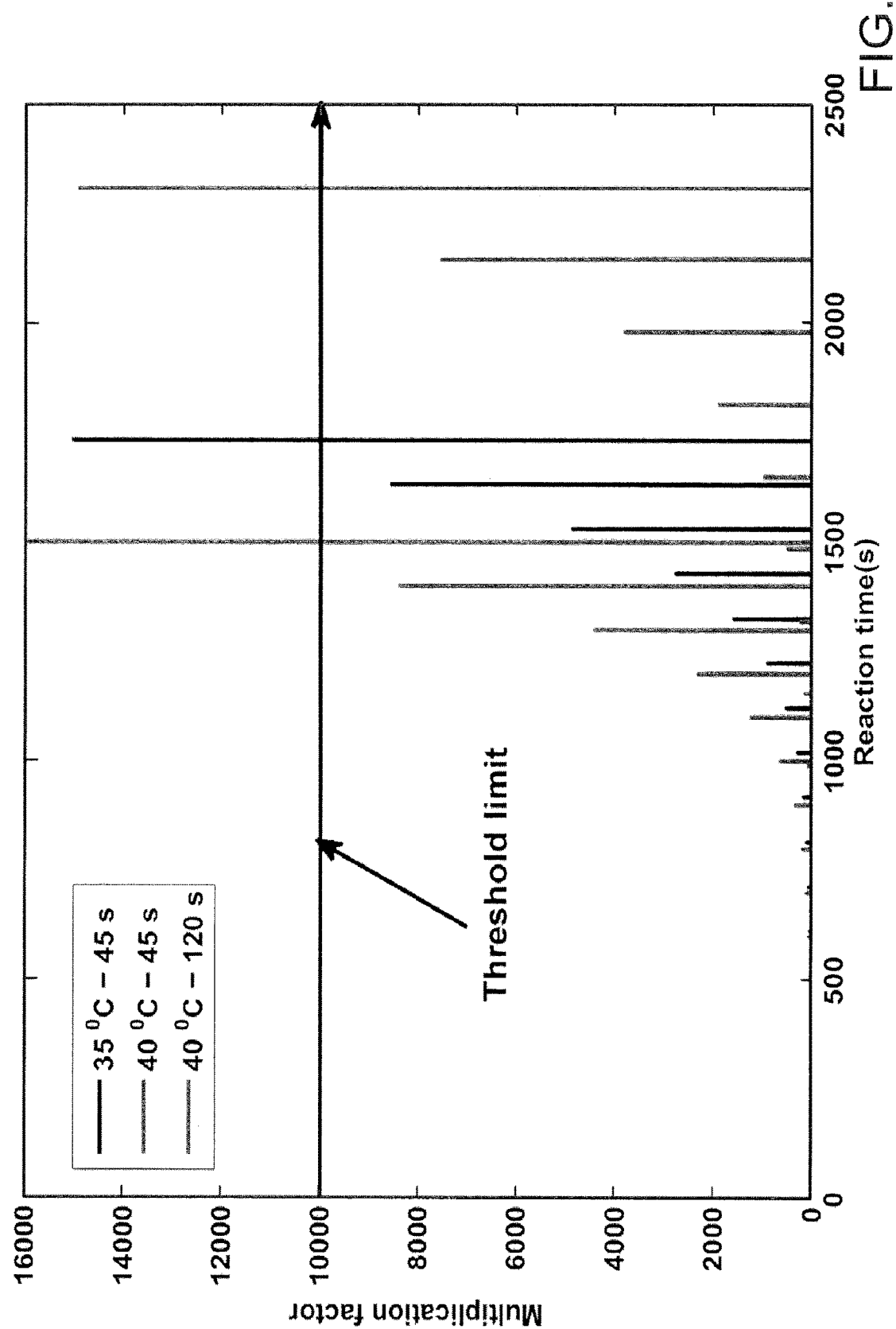

FIG. 15 compares the geometric growth of DNA with respect to reaction time under the above three reaction conditions.

Figure 16:
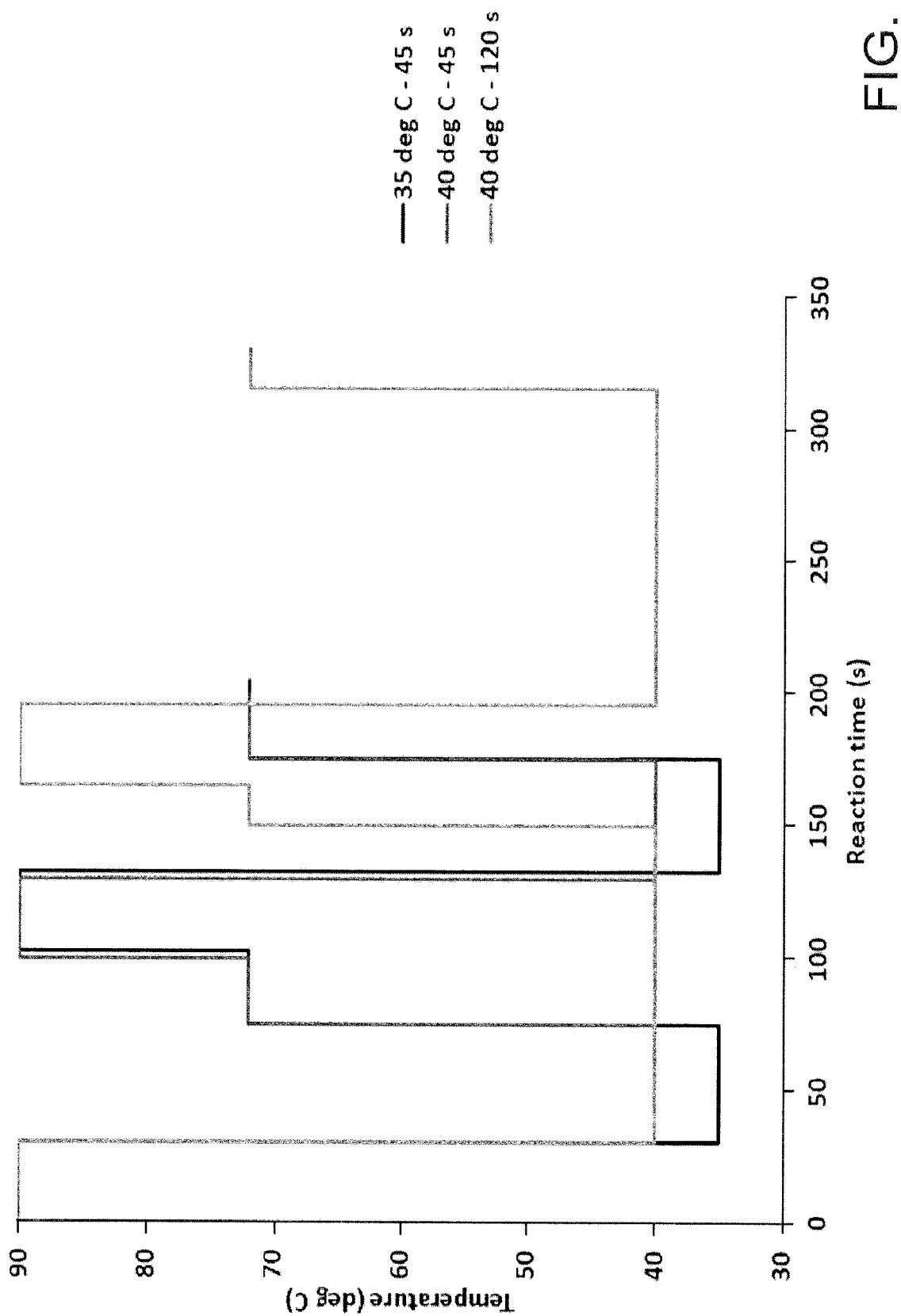

FIG. 16 illustrates the modified temperature protocol based on this analysis.

Figure 17:
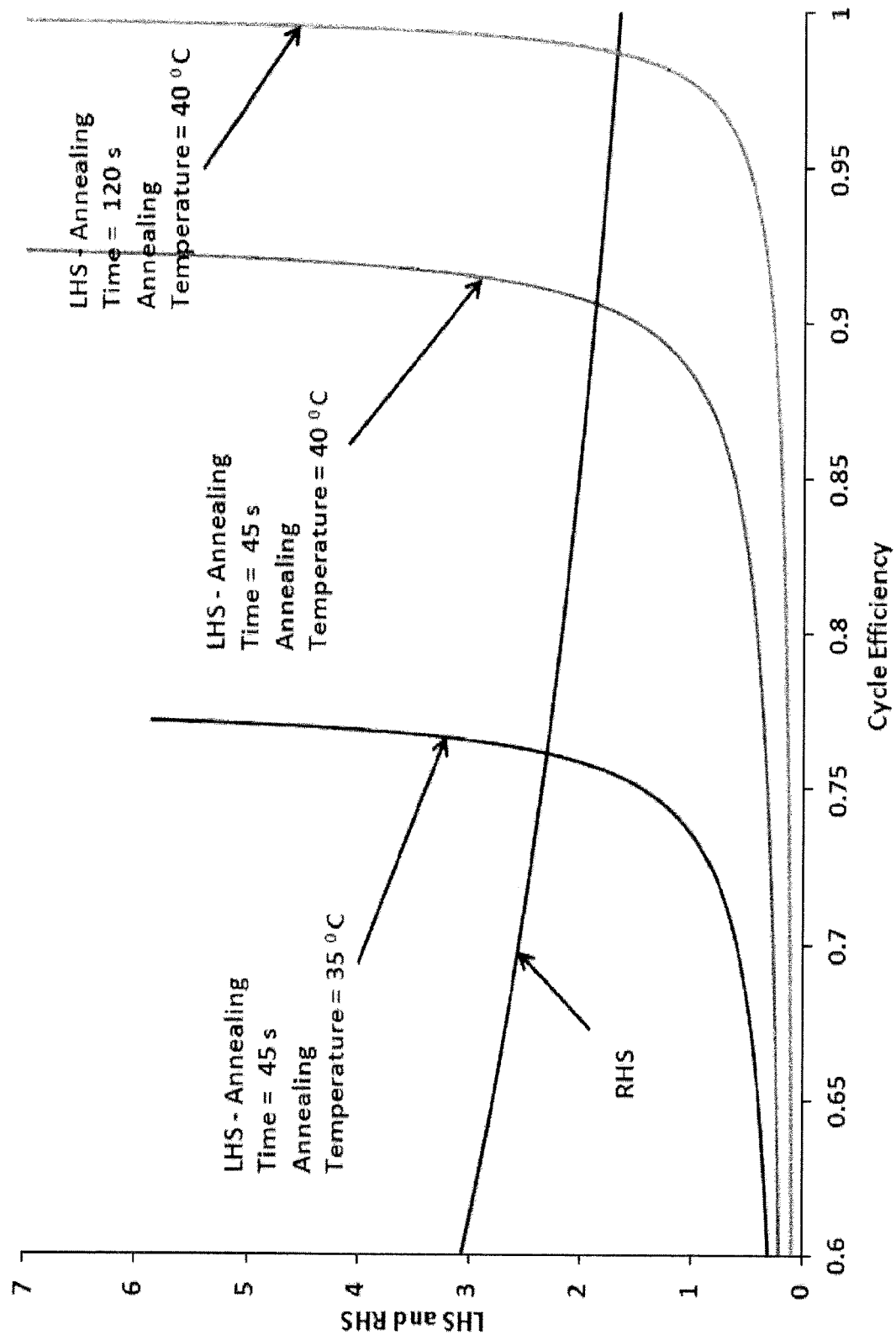

FIG. 17 illustrates optimal cycle efficiency at the three different reaction conditions.

FIG. 18 provides g(x) for a simplex PCR with n=2.

Figure 19:
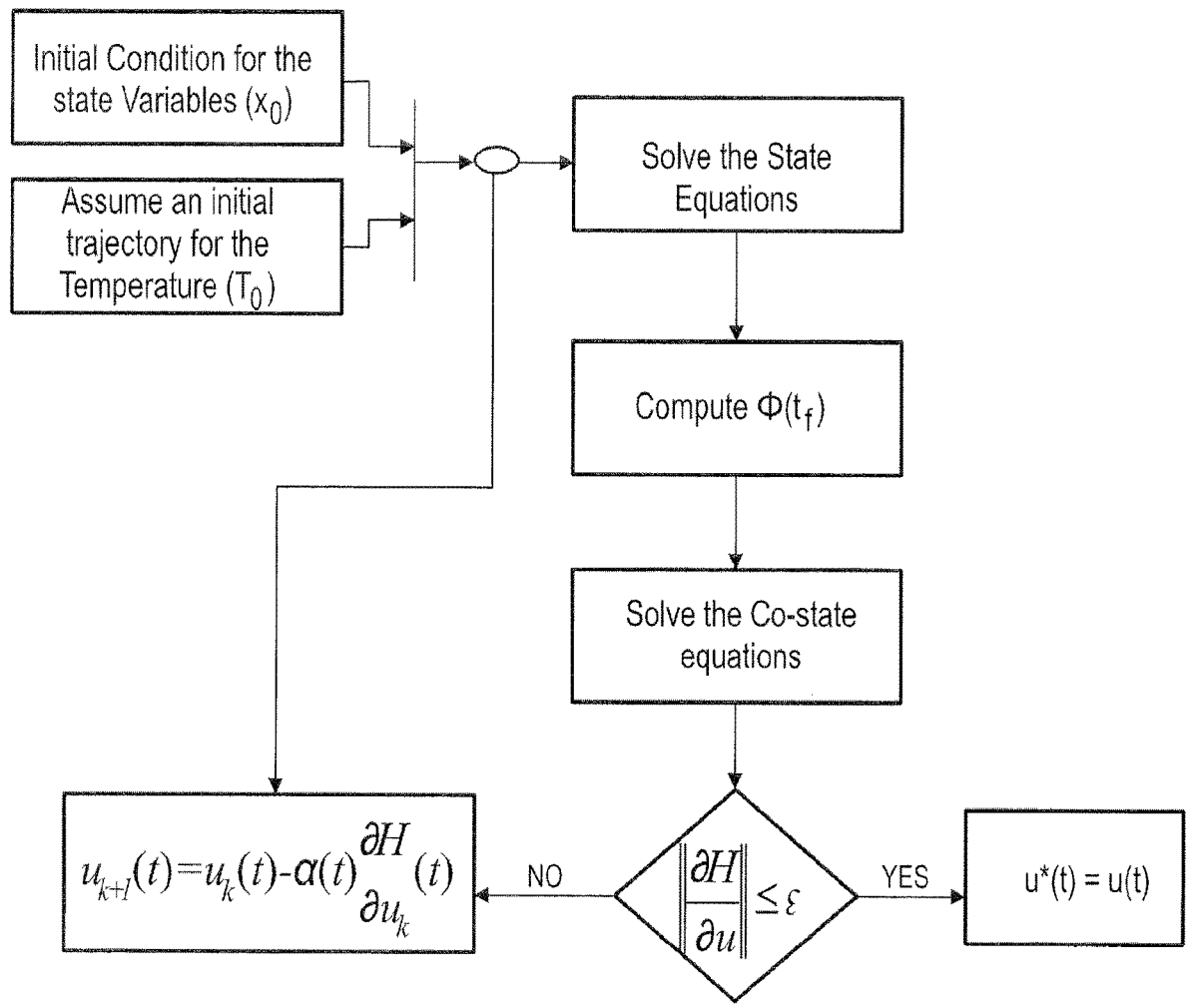

FIG. 19 illustrate control vector iteration to solve the optimal control problem.

Figure 20:
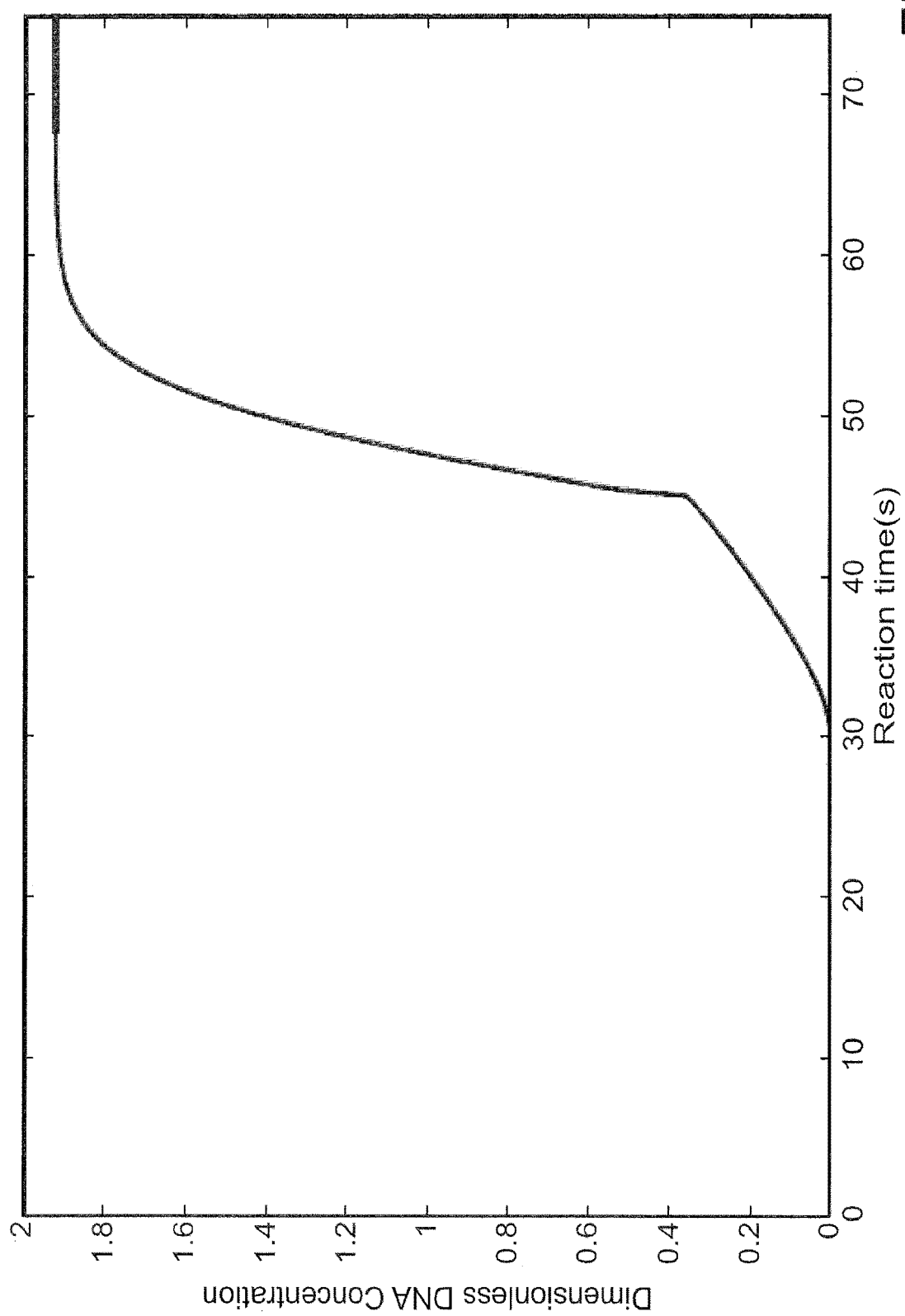

FIG. 20 illustrates the optimal DNA concentration profile obtained by solving PCR optimal control problem using control vector iteration according to one embodiment described herein.

Figure 21:
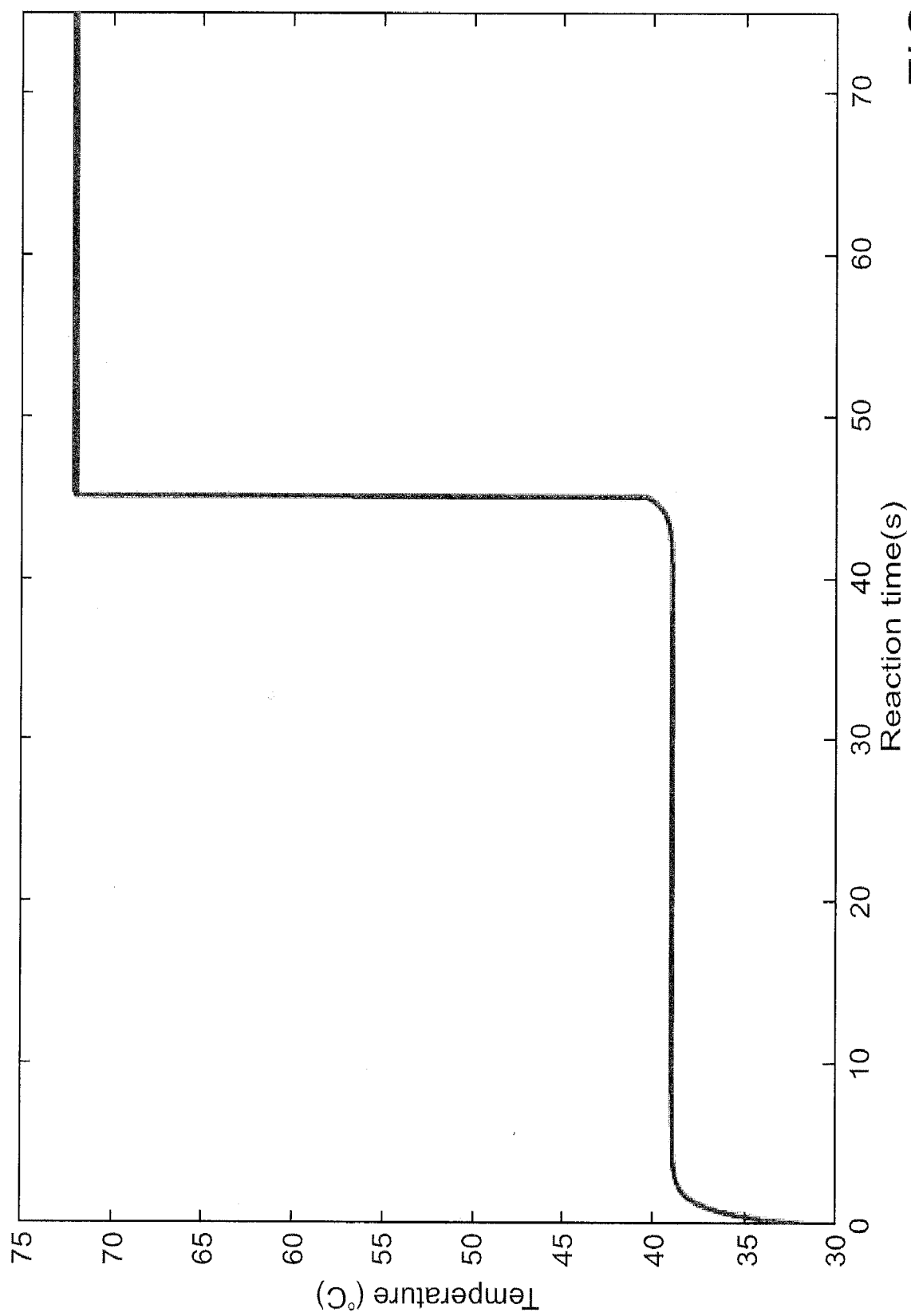

FIG. 21 illustrates the optimal temperature profile obtained by solving PCR optimal control problem using control vector iteration according to one embodiment described herein.

FIGS. 22(a)-(b) illustrate the convergence of an algorithm for solving PCR optimal control problem according to one embodiment described herein.

FIG. 23 illustrates the predicted evolution of reaction species during a typical primer annealing reaction

DETAILED DESCRIPTION

Embodiments described herein can be understood more readily by reference to the following detailed description and examples and their previous and following descriptions. Elements, apparatus and methods described herein, however, are not limited to the specific embodiments presented in the detailed description and examples. It should be recognized that these embodiments are merely illustrative of the principles of the present invention. Numerous modifications and adaptations will be readily apparent to those of skill in the art without departing from the spirit and scope of the invention.

I. Annealing Efficiency

Methods described herein, in some embodiments, can enhance annealing efficiency for first and second strands of DNA over a predetermined time period or at a predetermined temperature. In some embodiments, a computer implemented method for enhancing annealing efficiency of first and second single strands of deoxyribonucleic acid (DNA) over a predetermined time period is described herein, the method comprising accessing a memory via a computing device processor, wherein the memory comprises computer instructions that when operated by the computing device processor cause the computing device processor to receive information comprising sequences of the first and second DNA strands, concentrations of the first and second DNA strands, length of the predetermined time period and a set of annealing reaction temperatures; determine the forward reaction rate constant, $k_f$, of annealing the first and second single strands of DNA at annealing reaction temperatures in the set; determine the reverse reaction rate reaction rate constant, $k_r$, of annealing the first and second single strands of DNA at annealing reaction temperatures in the set; and select one or more of the annealing reaction temperatures sufficient to produce a DNA concentration from the annealed first and second strands in excess of a predetermined threshold within the predetermined time period.

A non-limiting example is now presented to further illustrate the foregoing method enhancing annealing efficiency. The computer readable instructions cause the computing device to receive information comprising sequences of the first and second DNA strands, concentrations of the first and second DNA strands, length of the predetermined time period and a set of annealing reaction temperatures. This data in the present non-limiting example is provided in Table I.

TABLE I

Information received by the processor

| Information Category | Assigned Value |
| --- | --- |
| Sequence 1$^{st}$ DNA strand | $A_{10}$ |
| Sequence 2$^{nd}$ DNA strand | $U_{10}$ |
| Concentration 1$^{st}$ DNA strand | 40 μM |
| Concentration 2$^{nd}$ DNA strand | 40 μM |
| Length of predetermined time period | 1 s |
| Set of annealing reaction temperatures | 3.4° C., 7.7° C., 12.6° C., 16.9° C. and 23.3° C. |

From this data set, the forward reaction rate constant, $k_f$, and the reverse reaction rate constant, $k_r$, are determined in terms of the equilibrium constant and relaxation time for DNA hybridization as follows. First, $k_f/k_r$ is expressed as $K_{eq}(T)$, which is determined according to the equation (1):

$$K_{eq}(T) = \exp\left(\frac{-\Delta G(T)}{RT}\right) = \frac{k_f}{k_r[C_0]} \quad (1)$$

wherein ΔG of the entire sequence (here $A_{10}:U_{10}$) is obtained from the nearest neighbor (NN) method for DNA melting thermodynamics. The nearest neighbor method provides the ΔG for pairs of nucleotide bases in the input sequence (here AA:UU). The ΔG for the entire sequence employed in the expression of $K_{eq}(T)$ is obtained by summation of these free energies and correction factors for end effects.

σ(T) is a resistance to formation of the first few base pairs, which constitute the hybridization nucleus. Following determination of $K_{eq}(T)$, σ(T) is obtained according to the equation (2):

$$K_{eq}(T) = \sigma(T)\left(\prod_{i=1}^{N} s_i(T)\right) \quad (2)$$

Wherein N denotes the sequence length (here 10), each $s_i$ is determined according to the nucleotide base pair as set forth in equations (3) and (4).

$$s_{AT}(T) = 1.04 \times 10^{-5} \exp\left(\frac{8000}{RT}\right) \quad (3)$$

$$s_{CG}(T) = 1.04 \times 10^{-5} \exp\left(\frac{8000}{RT}\right) \quad (4)$$

As provided in equation (2), the $s_i$ values are multiplied to obtain the product $\Pi_{i=1}^{N} s_i(T)$ and σ(T) is solved for using the product $\Pi_{i=1}^{N} s_i(T)$ and the value of $K_{eq}(T)$ determined above according to equation (1).

Figure 1:
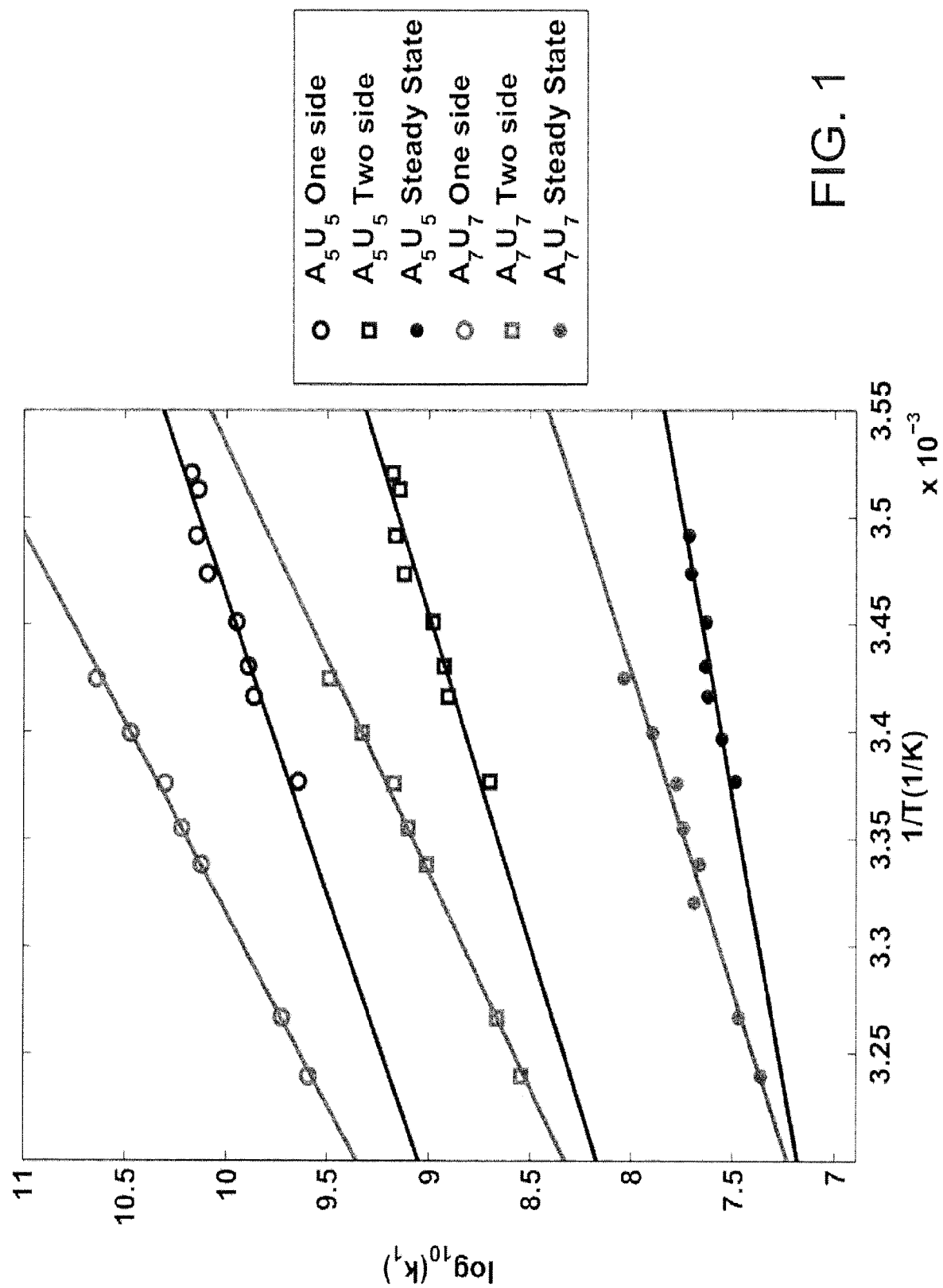
FIG. 1 illustrates the effect of temperature on forward rate constant, $k_1$, of each step of oligonucleotide hybridization reaction.

With σ(T) determined, $k_1(T)$, the forward rate constant for hybridization of a single base pair, is next obtained in order to set up a state space matrix for determining relaxation time, τ, for strand hybridization. Depending on DNA strand/sequence length, $k_1$ can be obtained by various methods. For sequence lengths of up to 14 bases, $k_1(T)$ can be obtained from a plot such as that illustrated in FIG. 1. FIG. 1 illustrates the effect of temperature on the rate constant, $k_1$, for several different sequence lengths. More generally, $k_1(T)$ for any given nucleotide sequence length can be estimated using experimental data, as will be described further below in this example.

Figure 2:
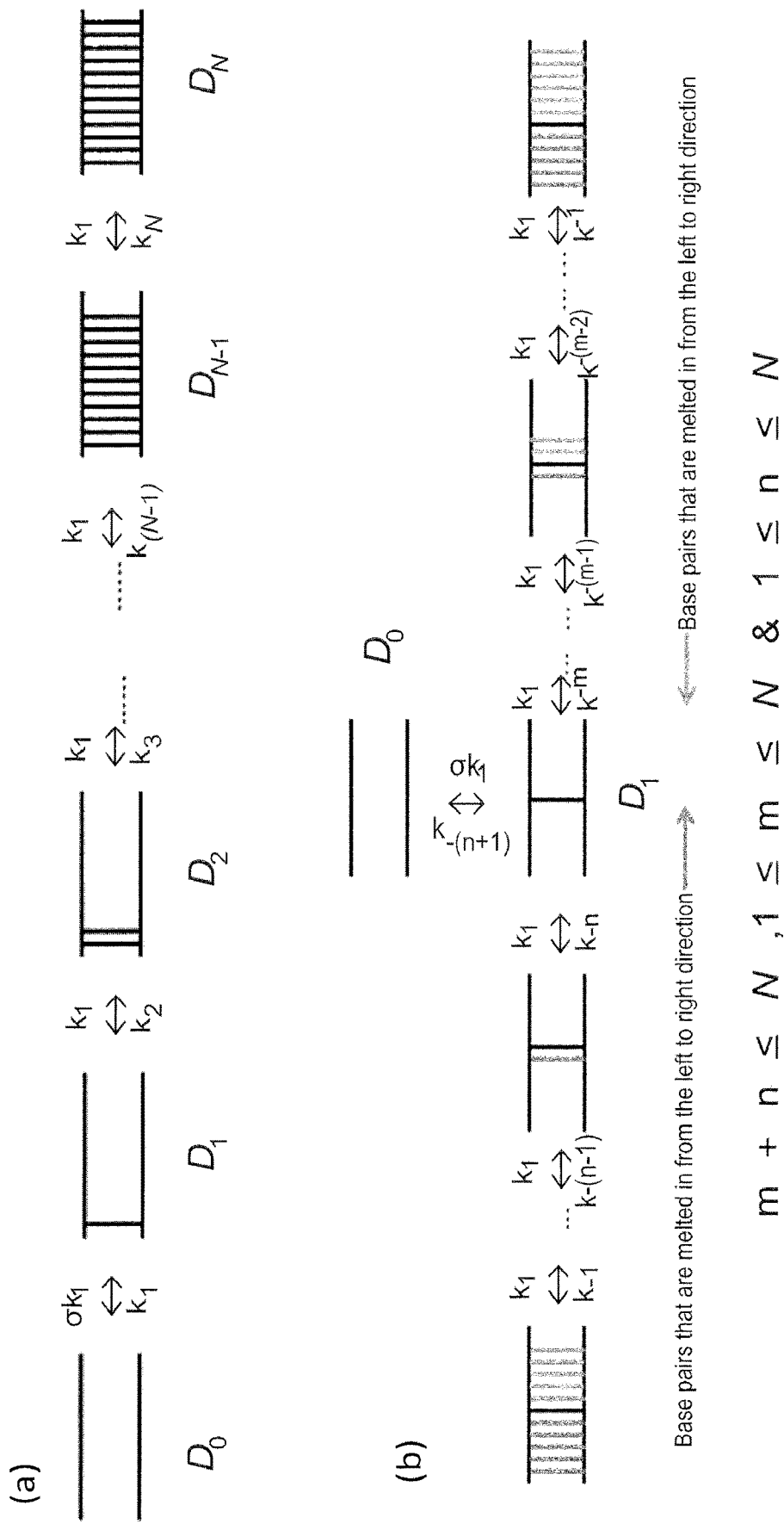
FIG. 2 illustrates (a) one-sided and (b) two-sided melting in conjunction with reaction mechanism $R_1$ described herein.

The relaxation time for a given oligonucleotide sequence, which is the characteristic time constant for the system to return to equilibrium after a perturbation from equilibrium, can be calculated based on either one-sided or two-sided oligonucleotide melting models. FIG. 2 illustrates one- and two-sided melting. A detailed unsteady state balance of the chemical reaction network for DNA hybridization yields a set of coupled first order differential equations after linearization around the equilibrium:

$$\frac{dx}{dt} = Ax, \; x(0) = x_{init}$$

where x denotes the vector of deviations of individual base pair concentrations from equilibrium. In one-sided melting, the matrix A takes the form $$A = \begin{bmatrix} -\sigma[D_{0eq}]k_1 & k_{-0} & 0 & 0 & \cdots \\ \sigma[D_{0eq}]k_1 & -k_1-k_{-0} & k_{-1} & 0 & \cdots \\ 0 & k_1 & -k_1-k_{-1} & k_{-2} & \cdots \\ 0 & 0 & k_1 & -k_{-2} & \cdots \\ \vdots & \vdots & \vdots & \vdots & \ddots \end{bmatrix}$$

Two-sided melting models, which allow melting to occur simultaneously from both sides of the sequence, are the most accurate. The reaction mechanism $R_1$ of the two-sided melting reaction is given below. For clarity, the mechanism for N=2 is presented.

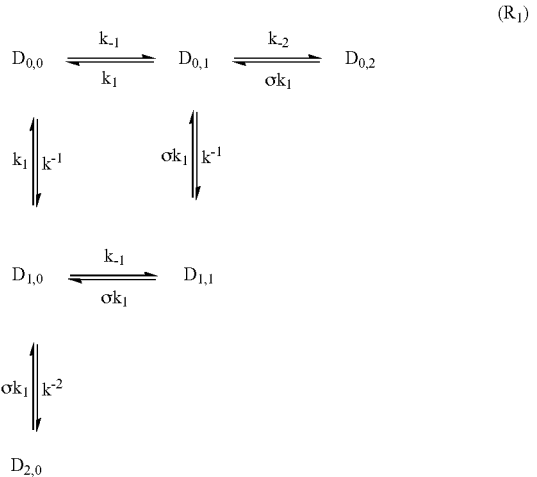

(R$_1$)

$D_{m,n}$ represents the state of a DNA molecule where m and n denote the number of base pairs melted from left and right side of the DNA molecule respectively. In reaction $R_1$, the horizontal direction represents right-sided melting and the vertical direction represents left-sided melting. The total number of possible states in an N base pair hybridization reaction is (N+1)×(N+2)/2. Out of these, there are N states that have only one base pair hybridized, in N different positions. The σ parameter is associated with the rate constant for formation of each of these N states. The number of states in one-sided melting is of O(N), whereas in the two-sided melting model, it is of O(N²). Using the convention that states with the same m value are grouped together, the state vector for two-sided melting is:

$$x=[D_{0,0},D_{0,1},D_{0,2},D_{1,0},D_{1,1},D_{2,0}]^T$$

and the state space matrix for the reaction $R_1$ is:

$$A = \begin{bmatrix} -(k^{-1}+k_{-1}) & k_1 & 0 & k_1 & 0 & 0 \\ k_{-1} & -(k_{-2}+k^{-1}+k_1) & \sigma[D_{0,2eq}]k_1 & 0 & \sigma[D_{1,1eq}]k_1 & 0 \\ 0 & k_{-2} & -\sigma[D_{0,2eq}]k_1 & 0 & 0 & 0 \\ k^{-1} & 0 & 0 & -(k_{-1}+k^{-2}+k_1) & \sigma[D_{1,1eq}]k_1 & \sigma[D_{2,0eq}]k_1 \\ 0 & k^{-1} & 0 & k_{-1} & -2\sigma[D_{1,1eq}]k_1 & 0 \\ 0 & 0 & 0 & k^{-2} & 0 & -\sigma[D_{2,0eq}]k_1 \end{bmatrix} \quad (5)$$

Each diagonal block of this two-sided melting matrix corresponds to melting from the right side with a constant number m of base pairs dissociated from the left side. In the two-sided melting mechanism, there are N+1 states representing fully dissociated single-stranded DNA (m+n=N). These can be represented using one notation, $D_{0,N}$. In doing this, rates that we counted twice in the above state space matrix (5) are corrected. For example, reaction $R_1$, $D_{1,0}$ gives $D_{1,0}$ and $D_{2,0}$, which represent the single-stranded state. Hence, the disappearance rate of the molecule $D_{1,0}$ has been counted twice. Thus, from the above state matrix (A), two redundant states (in general N states) should be removed and the rates that were counted twice should also be corrected to obtain the correct state space matrix for two-sided melting. Note the total number of states (N+1)×(N+2)/2−N. Therefore, the Corrected Reaction Mechanism (CRM) $R_2$ for two-sided melting (considering N−2) is given as:

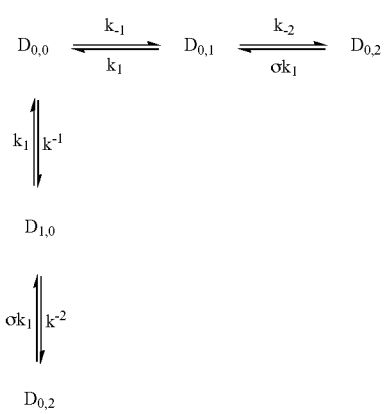

(R₂)

The state space matrix for two-sided melting (N=2) based on the above modified reaction mechanism is thus given by:

$$A = \begin{bmatrix} -(k^{-1}+k_{-1}) & k_1 & k_1 & 0 \\ k_{-1} & -(k_{-2}+k_1) & 0 & \sigma[D_{0,2eq}]k_1 \\ k^{-1} & 0 & -(k^{-2}+k_1) & \sigma[D_{0,2eq}]k_1 \\ 0 & k_{-2} & k^{-2} & -2\sigma[D_{0,2eq}]k_1 \end{bmatrix} \quad (6)$$

$$x = [D_{0,0}, D_{0,1}, D_{1,0}, D_{0,2}]^T$$

The relaxation time, τ, can be calculated from the state matrix (6). For example, with σ(T) determined for A10:U10 as described above, $k_1$ determined from FIG. 1, state space matrix (6) is solved for the largest eigenvalue, $\lambda_{max}$. $\lambda_{max}$ is related to τ though equation (7):

$$\tau = -1/\lambda_{max} \quad (7)$$

Figure 3:
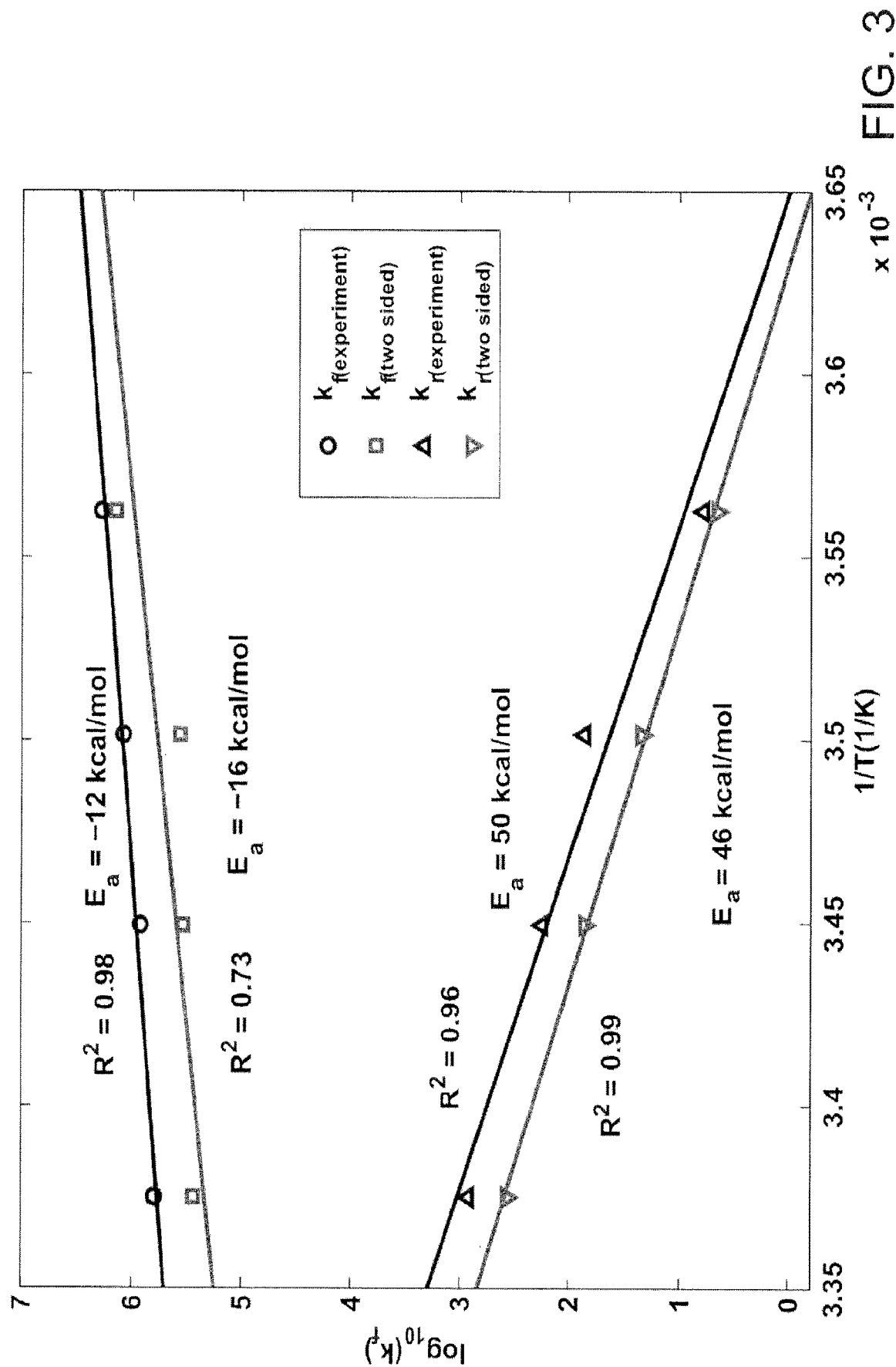
FIG. 3 illustrates comparison between theoretically and experimentally estimates forward ($k_f$) and reverse ($k_r$) for single stranded ($S_1$, $S_2$) hybridization reaction.

With the relaxation time now obtained, $k_f$ and $k_r$ are obtained by simultaneously solving equation (1) in conjunction with equation (8):

$$\tau = 1/(k_f[S_{2eq}+S_{1eq}]+k_r) \quad (8)$$

wherein $S_{1eq}$ and $S_{2eq}$ are equilibrium concentrations of the first and second DNA single strands. FIG. 3 illustrates comparison between theoretically and experimentally estimates forward ($k_f$) and reverse ($k_r$) for single stranded ($S_1$, $S_2$) hybridization reaction. With $k_f$ and $k_r$ known, DNA concentration in excess of a predetermined threshold can be determined for a set of annealing reaction temperatures within a predetermined time period according to equation (9):

$$d[D]/dt = k_f[S_1][S_2] - k_r[D] \quad (9)$$

Figure 4:
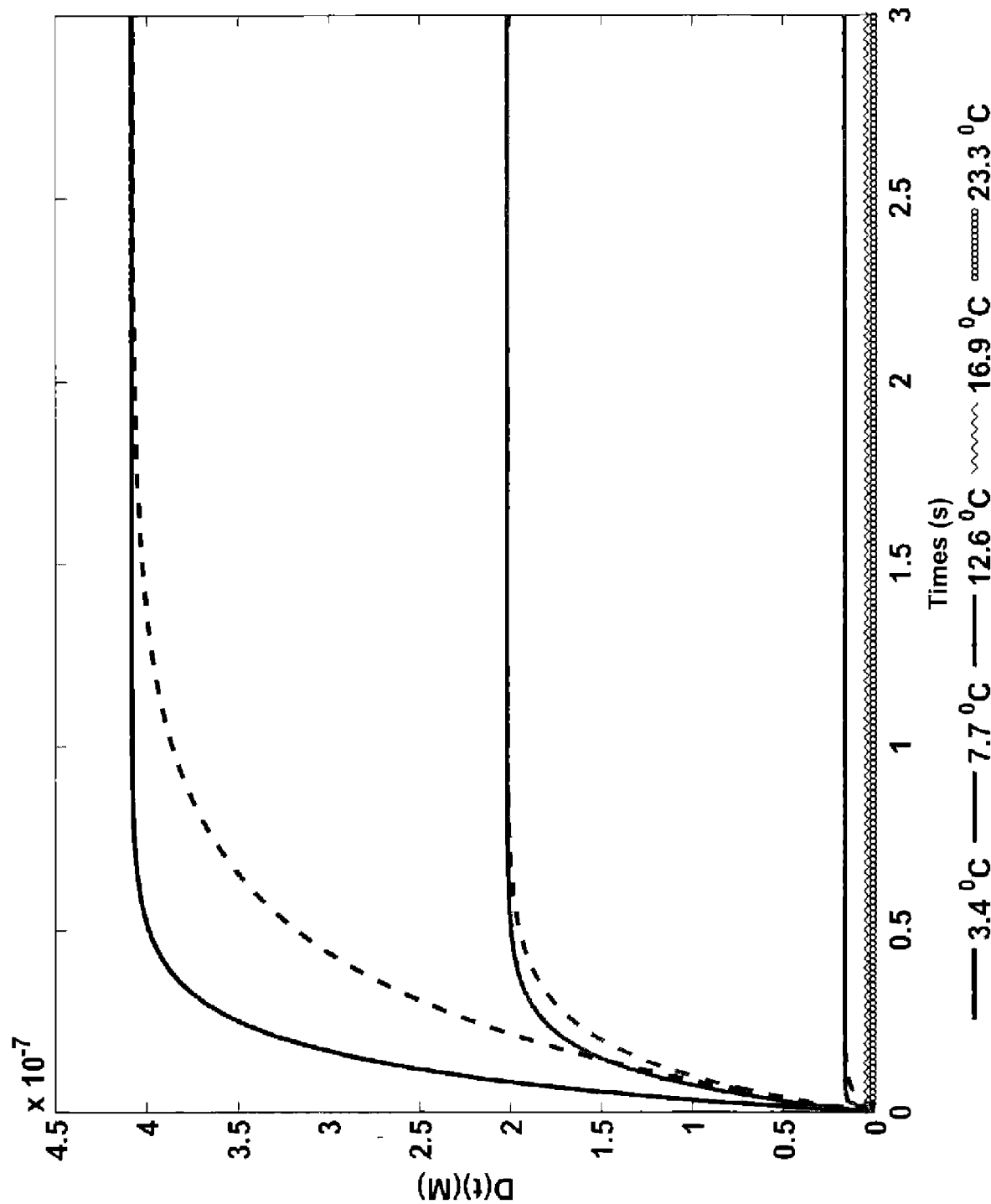
FIG. 4 illustrates determination of DNA concentration in excess of a predetermined threshold for a set of annealing reaction temperatures and time periods.
Figure 5:
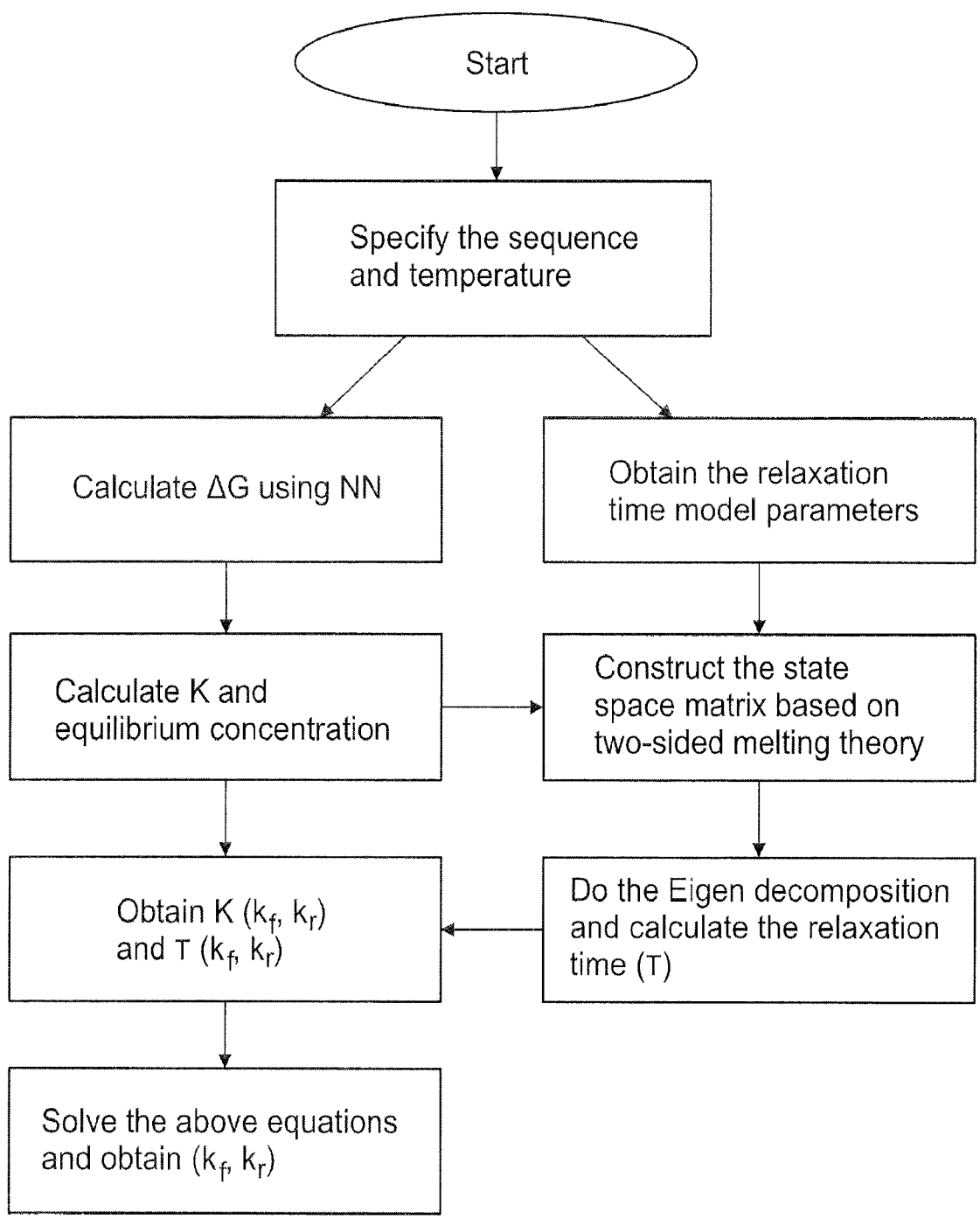
FIG. 5 is a flow chart detailing steps for determination of forward and reverse rate constants for DNA strand hybridization according to one embodiment described herein.

Similarly, DNA concentration in excess of a predetermined threshold can be determined for a set of annealing reaction time periods at a predetermined annealing reaction temperature according to equation (9). FIG. 4 illustrates determination of DNA concentration in excess of a predetermined threshold for a set of annealing reaction temperatures and time periods.

As noted above, $k_1(T)$ for DNA sequence length in excess of 14 bases can be estimated based on experimental data. Estimation of $k_1$ is a nonlinear parameter estimation problem in which a functional relationship between model parameters and experimentally measured dependent variable is available. For a known set of relaxation time vs. equilibrium concentration of single strands data, a least square objective function equal to the sum of squared differences between actual and predicted relaxation time can be minimized to estimate $k_1$. Given a set of T vs. $[D_{eq}]$ data, such a parameter estimation problem can be formulated and $k_1$ can be estimated at a specific temperature. For a fixed temperature, when the number base pairs, N, of a given sequence increases, $k_1$ should increase. This can be explained with more physical arguments and reasoning. For a fixed temperature, a sequence with more base pairs is more stable than a sequence with less base pairs. The individual stability constant $s_i$ is equal to the ratio $k_1/k_{-i}$. Though at a fixed temperature, s is a constant since a shorter sequence should be higher and $k_{-1}$ should be lower than those of a long sequence. $k_1$ for the transient models can be calculated by using the characteristic equation of the state space matrix A, with the negative reciprocal of the relaxation time r substituted in it as the eigenvalue λ, for the functional relationship:

$$\tau = f([D]_{eq}, \sigma, s_{AT}, s_{GC}, k_1, N) \quad (10)$$

Since the state space matrix is relatively large, a bisection method is implemented that is described below to solve for $k_1$ based on the transient models.

Assume an interval, [a, b] for $k_1$. Note that at a, the eigenvalue of the A should be greater than the actual eigenvalue ($\lambda_{actual}$) and at b, it should be less than the actual eigenvalue.
Let c=(a+b)/2
Find the eigenvalue of A at c.
If ($\lambda_c - \lambda_{actual}$<0), b=c, else a=c
Repeat until ($\lambda_c - \lambda_{actual}$<0)≈0.

Figure 6:
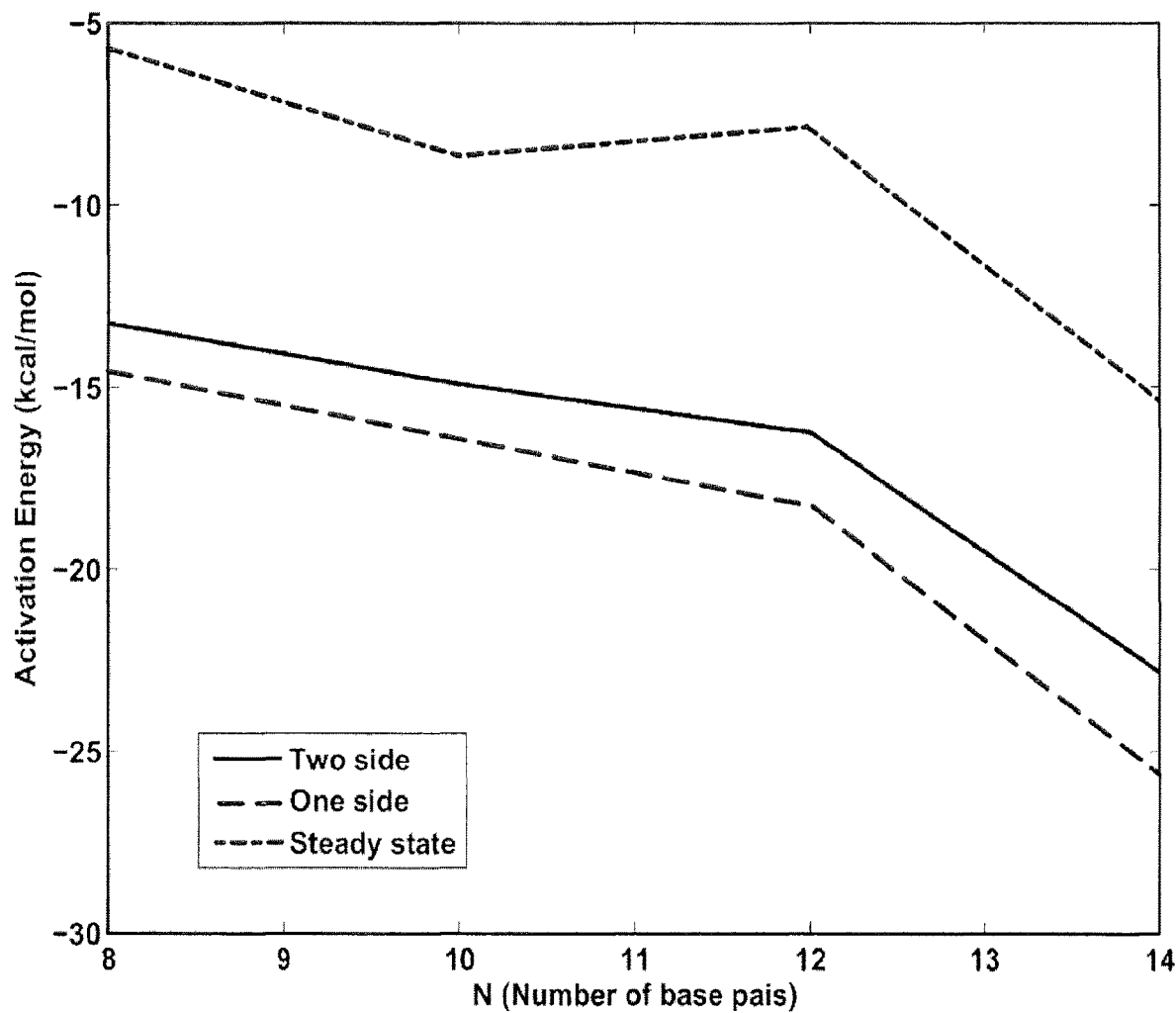
FIG. 6 illustrates variation of the activation energy of the single base pair forward hybridization reaction with respect the sequence length N.

Using the above algorithm for the transient models for the steady state model, $k_1$ was determined for four different (self-complementary) sequences A4U4:A4U4, A5U5:A5U5, A6U6:A6U6 and A7U7:A7U7, using their relaxation time and initial concentration of single strands data. FIG. 1 illustrates the variation of $k_1$ with respect to temperature for the sequences A5U5:A5U5 and A7U7:A7U7. The variation of apparent rate constant $k_1$ with respect to temperature follows an Arrhenius relationship, and it is similar to $k_f$ with a negative apparent activation energy that is a function of actual activation energy and the heat of base pair formation. FIG. 6 illustrates the variation of the activation energy for $k_1$ with respect to N. As detailed above, when N increases, $k_1$ increases, and hence the negative apparent activation energy decreases. For a fixed N, though a difference in apparent activation energy for homogeneous and heterogeneous sequences is expected, this difference may lie within an expected error bound. Therefore, a common $k_1$ can be estimated for heterogeneous sequences as long as their lengths are the same. More experiments can be conducted with different compositions and lengths of DNA sequences to estimate $k_1$ using least squares estimation rather than non-linear root finding.

II. PCR Amplification Efficiency

In another aspect, methods for enhancing amplification efficiency of a DNA sequence in one or more cycles of PCR are described herein. In some embodiments, a computer implemented method for enhancing amplification efficiency of a sequence of deoxyribonucleic acid (DNA) in a first cycle of polymerase chain reaction (PCR) is described herein, the method comprising accessing a memory via a computing device processor, where the memory comprises computer instructions that when operated by the computing device processor causes the computing device processor to (a) receive information comprising sequences of single strand DNA and primer, concentrations of the single strand DNA and primer, length of a predetermined time period for annealing the single strand DNA and primer and a set of annealing reaction temperatures; (b) determine the forward reaction rate constant, $k_f$, of annealing the single strand DNA and primer at annealing reaction temperatures in the set; and (c) determine the reverse reaction rate reaction rate constant, $k_r$, of annealing the single strand DNA and primer at reaction temperatures in the set. If desired, one or more of the annealing reaction temperatures sufficient to produce a primer hybridized DNA strand concentration in excess of a predetermined threshold within the predetermined time period for annealing can be selected. Alternatively, the extension kinetics described below can be determined and one or more of the annealing reaction temperatures required for production of DNA in excess of a predetermined threshold can be selected.

In some embodiments, the computing device further (a') determines a time period for duplex DNA melting sufficient to produce a concentration of single strand DNA in excess of a predetermined threshold. Additionally, in some embodiments, the computing device processor further (e) determines a time period for DNA extension sufficient to produce a concentration of DNA in excess of a predetermined threshold.

A. Primer-Template Annealing

As described above, a kinetic model of PCR includes kinetic models of melting, annealing, enzyme binding and extension reactions. Reaction $R_3$ represents an annealing reaction of the single strands (S) and primers (P).

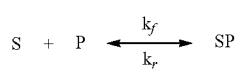

(R₃)

A procedure similar to that described in Section I above is employed to determine $k_f$, $k_r$ for S-P annealing and SP concentration at a set of reaction temperatures and times. The overall Gibbs free energy and hence the equilibrium constant $K_{annealing}$ for a given sequence at the chosen annealing temperature can be calculated using the NN model described in Section I herein.

$$K_{annealing} = \frac{k_f}{k_r} = \exp\left(-\frac{\Delta G_{annealing}}{RT}\right) \qquad (12)$$

Following determination of $K_{annealing}$, a state space matrix is established for determining annealing relaxation time. The state space matrix can be set up as described in Section I herein employing equations (2)-(4) and (5)-(6) in conjunction with reaction mechanisms $R_1$ and $R_2$. The state space matrix is solved for the largest eigenvalue, $\lambda_{max}$, and $\tau$ is obtained from equation (7). With the relaxation time now obtained, $k_f$ and $k_r$ are obtained by simultaneously solving equation (12) in conjunction with equation (13):

$$\tau = \frac{1}{k_f([S_{eq}] + [P_{eq}]) + k_r} \qquad (13)$$

wherein $P_{eq}$ and $S_{eq}$ are equilibrium concentrations of the primer and single stranded DNA. With $k_f$ and $k_r$ known, primer hybridized DNA strand concentration in excess of a predetermined threshold can be determined for a set of annealing reaction temperatures within a predetermined time period according to equation (14):

$$d[SP]/dt = k_f[S][P] - k_r[SP] \qquad (14)$$

Similarly, primer hybridized DNA strand concentration in excess of a predetermined threshold can be determined for a set of annealing reaction time periods at a predetermined reaction temperature according to equation (14). As described herein, $k_f$ and $k_r$ can be used solely for optimizing primer-DNA strand hybridization. FIG. 23 depicts the predicted evolution of reaction species for a typical primer annealing reaction with reaction temperature 20 deg C. and initial single strand and primer concentrations either 1 nM or 10 nM. Primer sequence 1 is 5' GCTAGCTGTAACTG 3' and primer sequence 2 is 5' GTCTGCTGAAACTG 3'. Alternatively, $k_f$ and $k_r$ can be used in conjunction with DNA extension rate constants in determining a temperature cycling profile for enhancing amplification efficiency of one or more cycles of PCR.

B. Enzyme Binding and Extension

Figure 7:
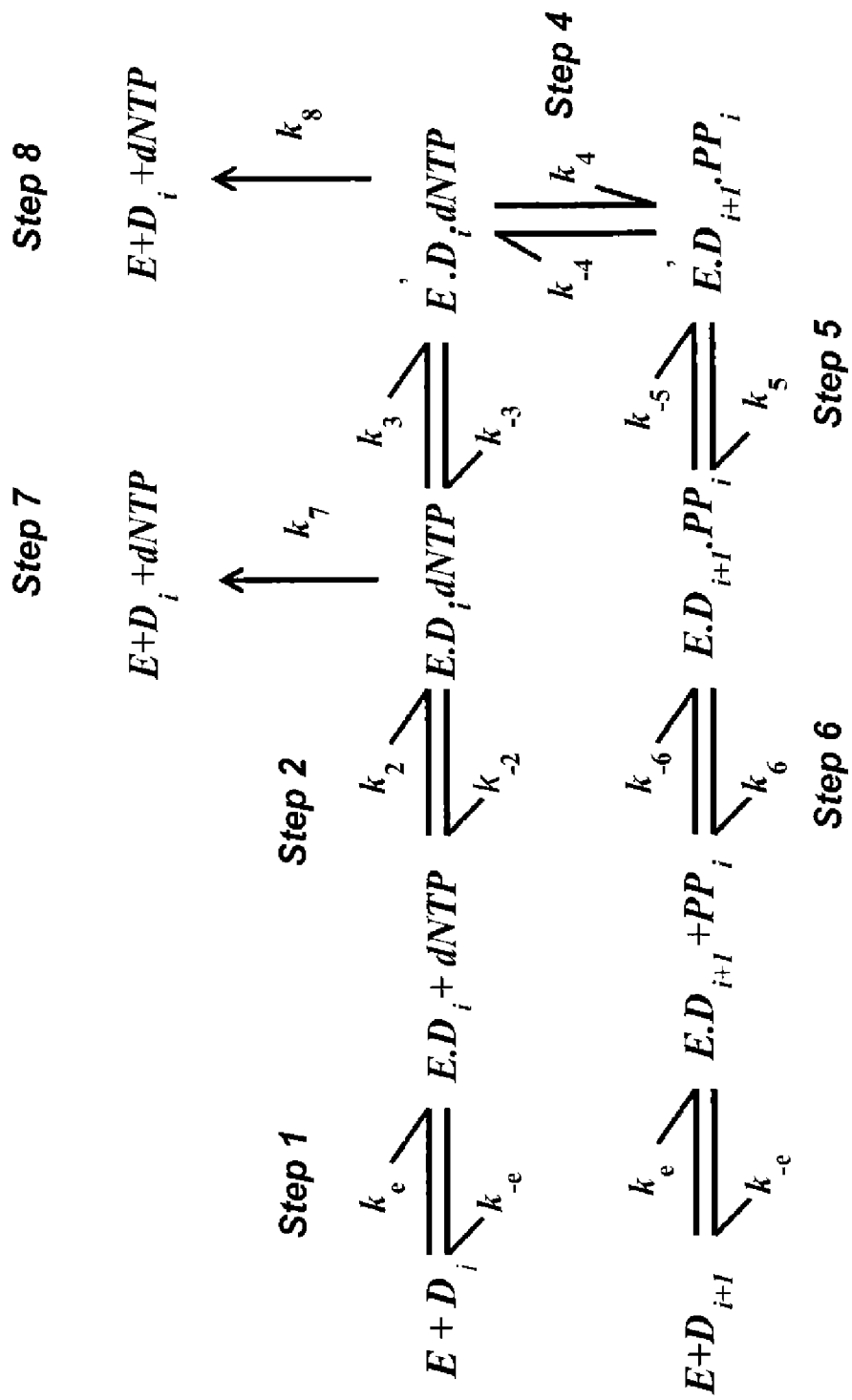
FIG. 7 represents a general reaction scheme for enzyme binding and extension reactions according to some embodiments described herein.

In the extension step, enzymatic addition of nucleotides converts the primer-template duplex (SP) into a complete dsDNA. There are several reaction mechanisms proposed for enzyme binding and extension reactions and FIG. 7 represents a general reaction scheme. In step 1, enzyme binds with $D_i$ molecule (primer-template with i added nucleotide bases) to form a binary complex $E.D_i$. In step 2, a deoxynucleotide triphosphate (dNTP) binds with $E.D_i$ to form a ternary complex, E.Di.dNTP, which undergoes a protein conformational change in step 3 and forms $E'.D_i.dNTP$. In step 4, a nucleotide is incorporated and a pyrophosphate molecule is released from $D_i$ and as a result $E'.D_{i+1}.PP_i$ is formed. $E'.D_{i+1}.PP_i$ undergoes a conformational change in step 5 leading to the formation of $E.D_{i+1}.PP_i$. In step 6, $PP_i$ is completely released from $E.D_{i+1}.PP_i$ and $E.D_{i+1}$ is formed. Finally the dissociation of $E.D_{i+1}$ produces $D_{i+1}$ and E. Besides these steps, there are parallel dissociation reactions represented by step 7 and 8 may also occur.

The final step 6 is irreversible with a rate constant $k_6$. Steps 3, 4 and 5 which are all a first order reversible reactions represent the conformational change of a ternary complex and their rate constants values are higher than $k_2$ and the forward rate constants of each step is higher than the reverse rate constant. Hence, the overall dynamics is controlled by step 2 which forms a ternary complex, $E.D_i.dNTP$ and the final step is irreversible.

The reaction mechanism of FIG. 7 can be represented using the simplified reaction schemes given by reaction

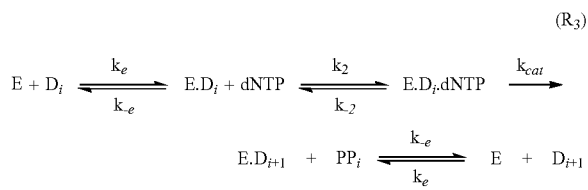

(R₃)

Figure 8:
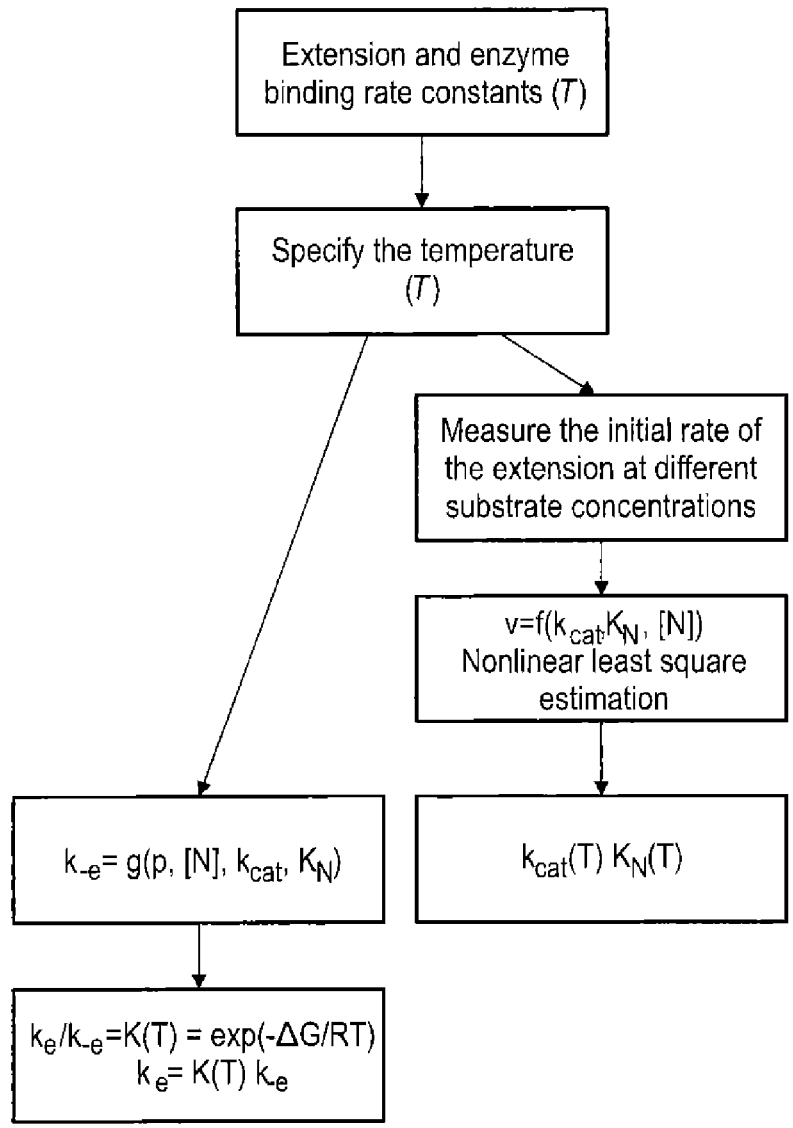
FIG. 8 identifies the steps involved in enzyme binding and extension model parameter estimation according to some embodiments described herein.

Kinetic parameters $k_e$, $k_{cat}$ and $K_N=(k_{-2}+k_{cat})/k_2$ in $R_3$ can be estimated for any polymerase using polymerase processivity and initial rate experiments and these temperature-dependent rate constants can be used, for example, to determine the optimal extension time(s) that minimizes the total PCR reaction time required to reach a predetermined threshold concentration of DNA. FIG. 8 identifies the steps involved in enzyme binding and extension model parameter estimation according to some embodiments described herein. For the present analysis, the themostable DNA polymerase is *Thermus aquatics* (Taq) polymerase.

1) Taq Reaction Rates ($K_N$, $k_{cat}$): Michaelis Menten Kinetics

In order to accurately evaluate the intrinsic kinetics of Taq, an experimental framework to quantify the rate of dNTP incorporation is established. In particular, a DNA substrate that represents a typical substrate in PCR applications and does not form secondary structure is employed.

Previous reports on DNA polymerase kinetics mostly employed two broad classes of substrates: a) activated genomic DNAs namely, the activated salmon sperm DNA or the activated Calf thymus DNA and b) primed M13 ssDNAs containing different primers. However, neither the M13 ssDNA nor the activated salmon sperm DNA represent typical substrates used in PCR or other biotechnology processes. In the majority of polymerase reactions the substrate is small to medium length ssDNA template (50 to 500 bases)—annealed generally to a small (10 to 20 bases long) open-ended (unobstructed for extension at the 3' end) oligomeric primer. Activated salmon sperm and calf thymus DNAs are large genomic DNA, with extension sites flanked and/or blocked by large duplex structures. Polymerase assisted dNTP incorporation in this substrate involves gap filling and strand replacement extensions. This type of extension processes is not typical of common applications of the polymerase extension reactions like the PCR. For different reasons, the large M13 ssDNA templates with molecular size of the order of 7.25 kilobases, also do not represent common PCR templates. It is likely that such a large genomic DNA will harbor secondary structures, which, if present, would inhibit or slow down the extension reactions. Presence and prevalence of secondary structures that may fall on the path of the primer extension will depend on the location on the template where the primer is attached and as such differences in apparent extension rates would be expected based on particular pairs of primed M13 used in the experiments. As with templates, secondary structures in the primer may also interfere with extension reactions.

The above discussion points to the fact that intrinsic reaction rates of a DNA polymerase cannot be accurately determined by using either the activated salmon sperm DNA or a ssDNA/primer complex where either the ssDNA template or the primer are prone to forming secondary structures. In addition, in order that reaction kinetics can be studied both at lower and higher temperatures, such as temperatures ranging from 50° C. to 75° C., the primer should have a $T_m$ equal to or higher than the than the highest temperature to be studied. These difficulties are overcome by using a synthetic template-primer pair, comprising of a 80-mer synthetic ssDNA with an overall GC content of 47.5% and designed to show minimal secondary structure and yet containing a 17-nucleotide stretch of high GC-containing sequence to accommodate a complementary 17-mer primer with high $T_m$ (88% GC, $T_m=80°$ C.), so that the kinetics of the reaction can be studied at different temperatures and up to or beyond the temperature at which the enzyme is supposed to exhibit its highest activity.

The single stranded TAT2 template (80 nt, 47.5% GC) was primed by using 7 equivalents of its 17-mer forward primer TAP1 (88% GC) in 1×Taq buffer (20 mM Tris-HCl, 50 mM KCl) containing 2 mM MgCl₂. The mixture was heated to 80° C. and cooled to room temperature by successively holding the temperatures and cooling as follows: hold at 95° C. for 1.5 minute, cool to 75° C. over 30 minutes, hold at 75° C. for 5 minutes (for slow primer annealing), cool to 70° C. over 20 minutes, cool to 45° C. over 45 minutes, and then cool to room temperature on the bench. The mixture was aliquoted in reaction tubes and Taq polymerase was added followed by dNTPs so that the final concentrations in each 20 µl reaction volume were 200 nM template (5.0 ng/µl), 1400 nM primer (7.24 ng/µl), 2 µM taq (0.056 U/µl) and various concentration of dNTPs. Studies of the bireactant Michaelis Menten (MM) reaction kinetics for Taq were performed at various extension temperatures from 55° C. to 75° C., at 5° C. intervals. Reactions at each temperature were setup with 12 different concentrations of dNTP ranging from 2-1000 µM while keeping free MgCl₂ concentration constantly at 2 mM, compensating for the chelation effect by dNTPs. Triplicate reaction tubes were first equilibrated in the CFX96 PCR machine at the extension temperature for 30 min before adding the dNTPs to start the reaction. Reactions were terminated at 0.33, 0.5, 0.67, 0.83, 1, 2, 3.5, 5, 6.5, 8.5 and 10 min by chilling to 4° C. and adding EDTA to a final concentration of 20 mM. Aliquots of 20 µl reaction mixture were then mixed with 80 µl of 1:178 dilution (in 1×TE buffer) of the PicoGreen Reagent. Fluorescence was measured in Fluoroskan Ascent Fluorescence 96/384 Well Plate Reader (485 nm excitation and 520 nm emission) after an incubation of 5 min at 37° C. The quantities of dNTP incorporated at each temperature and for each concentration were then plotted against time and the initial rates of the reactions at each temperature and each concentration were determined by fitting the reaction curve into a first-order reaction model.

Figure 9:
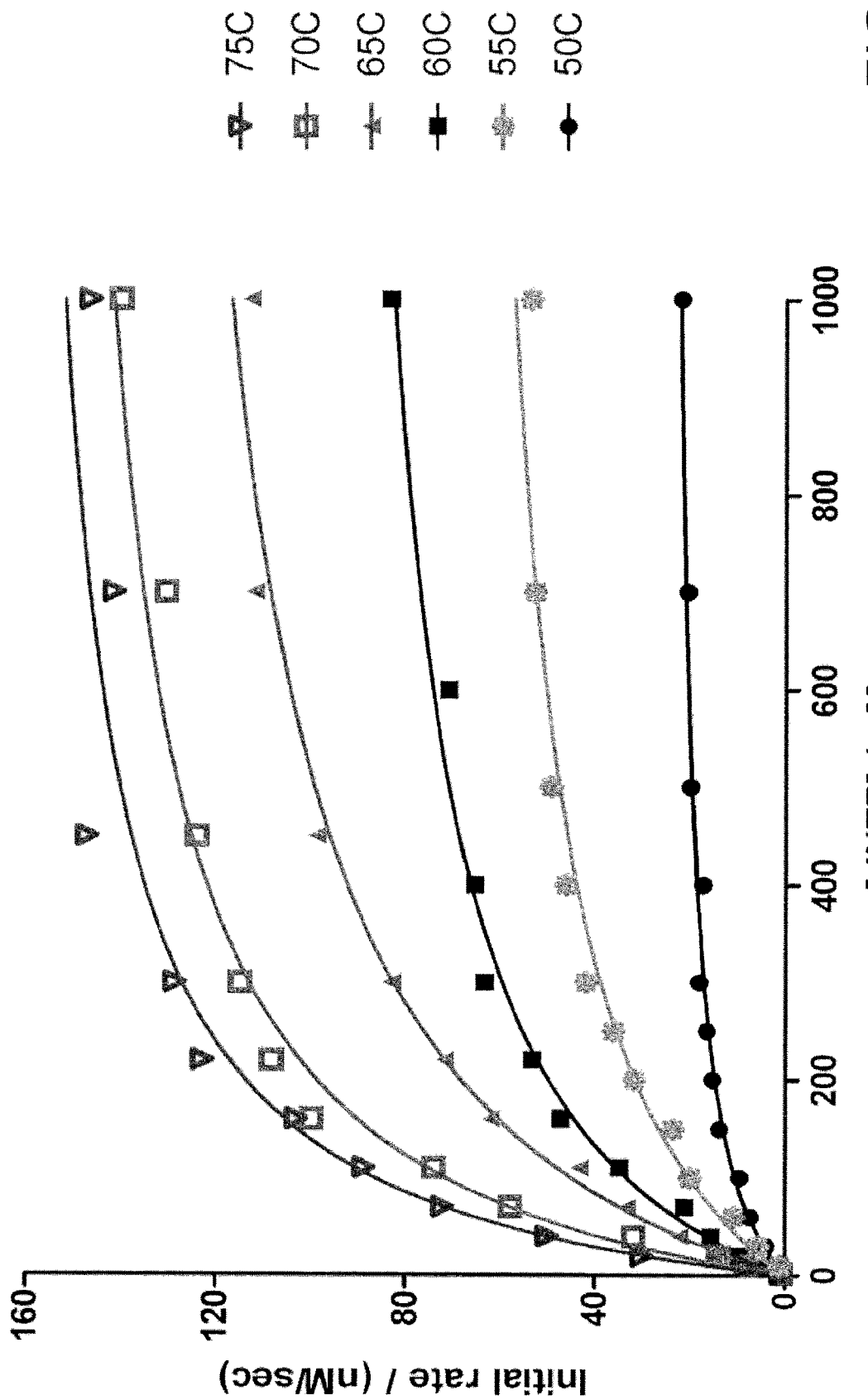
FIG. 9 illustrates the Michaelis-Menten plots of the activity of the Taq polymerase at various temperatures.

FIG. 9 illustrates the Michaelis-Menten plots of the activity of the Taq polymerase at various temperatures. The template used was the 80-mer synthetic ssDNA TAT2 annealed to a 17-mer ssDNA TAP1 at the 3'end. Both the template and the primer have been tested to be free of secondary structures. The individual points in the curves were obtained from time course experiments at each dNTP concentration at each temperature. The fluorescence intensity data was converted into nM of dNTP incorporated from a calibration curve. The kinetic parameters calculated from FIG. 9 are tabulated in Table 2. $k_{cat}$ denotes the catalytic rate constant for nucleotide addition and $K_N$ denotes the Michealis constant for nucleotide addition.

TABLE 2

Values of $K_N$; $k_{cat}$; and $k_{cat}/K_N$ for Taq polymerase at various temperature.

| Temperature/° C. | $K_N$/µM | $k_{cat}$/(sec⁻¹) | $k_{cat}/K_N$/(µM⁻¹ sec⁻¹) |
|---|---|---|---|
| 50 | 140 ± 10 | 12.7 ± 0.4 | 0.09 ± 0.01 |
| 55 | 250 ± 30 | 36 ± 2 | 0.14 ± 0.02 |

TABLE 2-continued

Values of $K_N$; $k_{cat}$; and $k_{cat}/K_N$ for Taq polymerase at various temperature.

| Temperature/° C. | $K_N$/μM | $k_{cat}$/(sec$^{-1}$) | $k_{cat}/K_N$/(μM$^{-1}$ sec$^{-1}$) |
|---|---|---|---|
| 60 | 200 ± 20 | 49 ± 2 | 0.25 ± 0.02 |
| 65 | 220 ± 20 | 71 ± 2 | 0.33 ± 0.03 |
| 70 | 120 ± 10 | 79 ± 3 | 0.65 ± 0.07 |
| 75 | 91 ± 8 | 83 ± 2 | 0.91 ± 0.09 |

Figure 10:
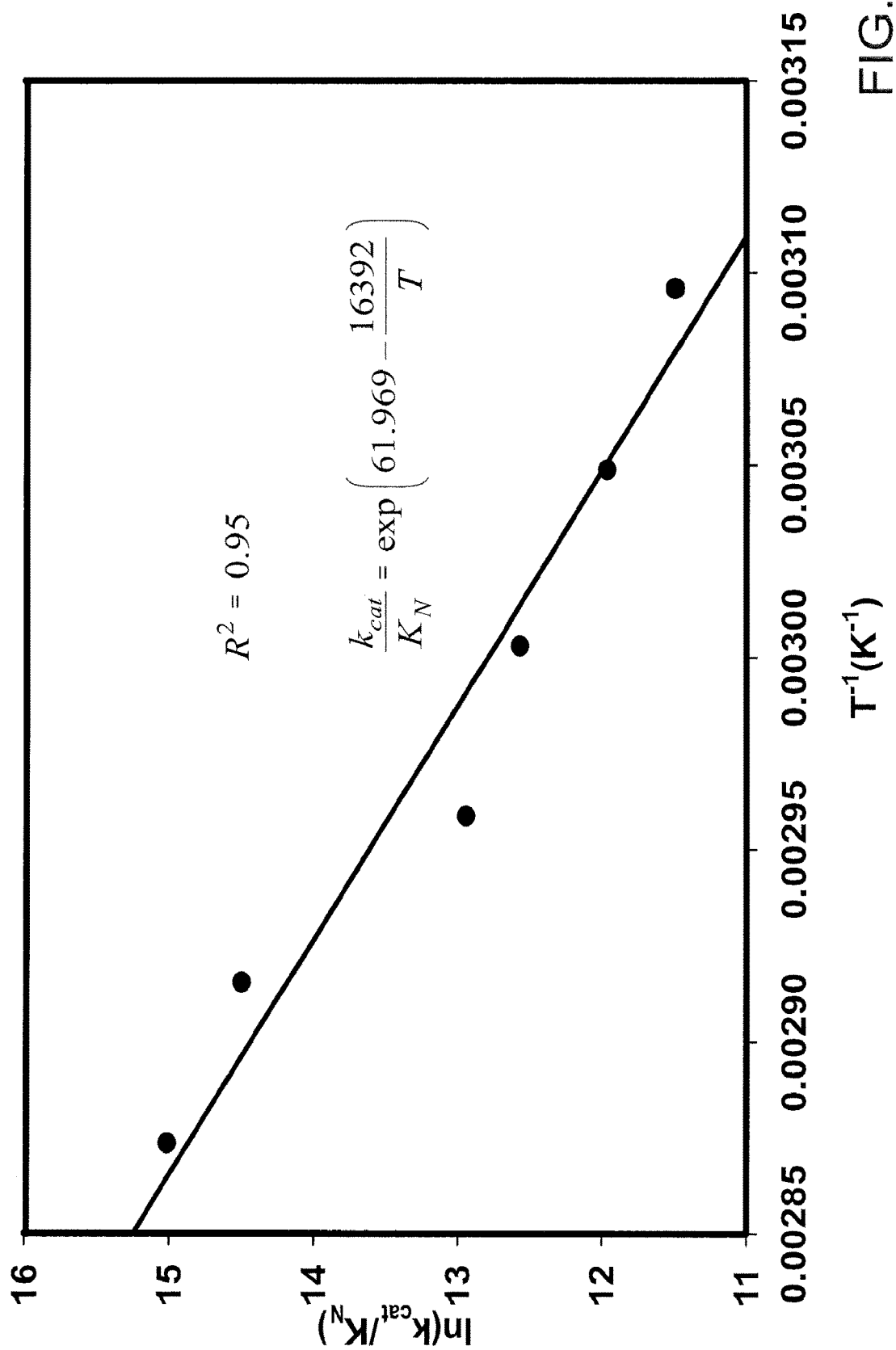
FIG. 10 provided temperature dependent extension rate constant $$\frac{k_{cat}}{K_N}$$

2) Calculate Kcat/Kn at the Desired Temperatures $$\frac{k_{cat}}{K_N}$$

for Taq polymerase is estimated at various temperatures based on the bireactants MM kinetics formulation above. FIG. 10 exhibits the temperature dependent apparent second order extension rate constant $$\frac{k_{cat}}{K_N}.$$

3) Run Single-Hit Condition Extension Experiments on the Polymerase at the Different Temperatures In single hit conditions, enzyme concentrations are sufficiently low that the probability of re-association is approximately zero. Therefore, they do not allow enzyme re-association. Hence enzyme-template association occurs only during the initial equilibration of enzyme with SP. Thus, the following reaction scheme for the addition of n base pairs is written

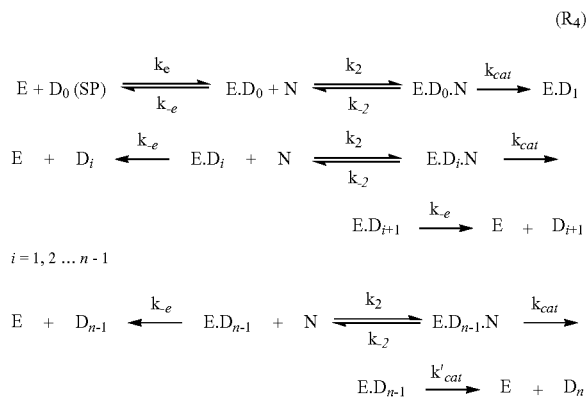

(R4)

$i = 1, 2 \ldots n - 1$

Single hit conditions are used to estimate polymerase processivity parameters. Processivity is defined as the average number of nucleotide incorporated per DNA-enzyme binding event. Gel electrophoretic analysis of the distribution of lengths of partially extended primer template DNAs Di in a single hit condition experiment provides the probability of dissociation of the polymerase at each position/time i, which can then can be used to calculate the processivity as described in 4).

4) Determine Processivity of the Polymerase

Let i index the sequence positions on the template. In a Markov chain formulation of dissociation, the index i at which dissociation occurs is denoted $i_{off}$. Let p denote the conditional probability of the polymerase not dissociating at position/time i, given that it was bound to the template at position/time i−1. The probability of dissociation at position/time i is then $$p_{off}(i) = (1-p)p^{1-i} \tag{15}$$

p is called the microscopic processivity parameter. The expected position of dissociation of the polymerase (expected stopping time) sometimes called the processivity, can be written as $$E[i_{off}] = \frac{1}{1-p} \tag{16}$$

$E[i_{off}]$ is generally reported as the processivity instead of the microscopic processivity parameter. The above expression is derived for a template of infinite length. Usually, in processivity experiments long templates are used to estimate p. For finite length, $$p_{off}(i) = 1 - \sum_{i=0}^{n-1} (1-p)p^{i-1}. \tag{17}$$

For heterogeneous templates, p will vary with position. From processivity experiments, one can obtain the p at each position since we will have $$p_{off}(i) = (1 - p_i)\prod_{j=0}^{i-1} p_j \; \forall \, i \tag{18}$$

These equations can be used to solve uniquely for each $p_i$. However, it is impractical to do processivity experiments for each new template. Hence, processivity experiments on templates with different types of nearest neighbor motifs (including hairpins) can be conducted for a given polymerase, and then nearest neighbor processivity parameters can be used in modeling of an arbitrary sequence.

The following Table provides the values of $E[i_{off}]$ and the conditions at which they are measured:

| Reference | Temperature (° C.) | Nucleotide concentration [N] (μM) | $E[i_{off}]$ |
|---|---|---|---|
| Wang et al (36) | 72 | 250 | 22 |
| Davidson et al (37) | 60 | 800 | 50-80 |

5) Relate $k_{-e}$ to Nucleotide Addition Rate Constants and Processivity

Now, at a fixed temperature, we seek a relationship between processivity of an enzyme and the rate constants of the reaction scheme $R_4$. In order to do this, we write the state space model for the reaction scheme $R_4$. We omit

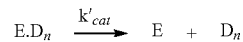

from the state space model for simplicity as it does not affect equilibrium and we are not estimating the corresponding rate constant. Since the substrate, dNTP, concentration is always in excess compared to enzyme, Michaelis-Menten (MM) kinetics is valid and hence the steady state assumption for the intermediate concentration is valid. Therefore, $$\frac{d}{dt}[E.D_i.N] = \tag{19}$$
$$-[E.D_i.N](k_{-2} + k_{cat}) + k_2[E.D_i][N] = 0 \Rightarrow [E.D_i.N] = \frac{[E.D_i][N]}{K_N}$$

where $$K_N = \frac{k_{-2} + k_{cat}}{k_2}.$$

Through analysis of the state space model, it is found that $$p = \frac{\frac{k_{cat}}{K_N}[N]}{\frac{k_{cat}}{K_N}[N] + k_{-e}}$$

Therefore $$\frac{k_{-e}}{\frac{k_{cat}}{K_N}[N] + k_{-e}} = 1 - p \Rightarrow k_{-e} = \frac{\frac{k_{cat}}{K_n}[N](1-p)}{p} \tag{20}$$

Equation (20) can be written as follows in tell is of processivity:

$$k_{-e} = \frac{k_{cat}}{k_N}[N]\left(\frac{1}{E[i_{off}] - 1}\right) \tag{21}$$

As per equation (21), if $$\frac{k_{cat}}{K_N}$$

and processivity of a polymerase is known at a specific temperature, it is possible to estimate $k_{-1}$ for any polymerase, equation (21) is valid under the approximations applied in the derivation of (R3). In equation (21) $k_{-e}$ and $$\frac{k_{cat}}{K_N}$$

are concentration independent terms and hence, the processivity $E[i_{off}]$ or the conditional probability p depends on [N].

Using the above values, $k_{cat}/K_N$ and equation (21), $k_{-e}$ at 60° C. and 72° C., has been estimated, respectively. The $k_{-e}$ for S. solfataricus P2 DNA polymerase B1(36) at 37° C. is known and the same value for Taq polymerase enzyme is employed as their equilibrium constants are of the same order of magnitude. Thus, $k_{-e}$ can be obtained at three different temperatures and hence an Arrhenius relationship is fitted as shown in FIG. 11 to estimate the temperature dependent dissociation rate constant $k_{-e}$. $k_{cat}$', the rate constant for dissociation of DNA from $E.D_n$ that is depicted in reaction scheme (R4), is approximated by $k_{-e}$.

6. Solve for $k_e(T)$

Equilibrium thermodynamic analysis for the polymerase enzyme binding reaction has been studied extensively with the *Thermus aquaticus* enzyme. Such studies estimated the temperature dependent equilibrium constant, which is the ratio of $k_e/k_{-e}$. Therefore, based on the temperature dependence of $k_{-e}$ and $K_{binding}$, $k_1$ has been estimated and its Arrhenius plot is shown in FIG. 12. For the specified extension temperature T and each of the extension times considered, the amount DNA produced by solving the system of extension rate equations for PCR is predicted, using the values of kcat/Kn (T), $k_e(T)$, and $k_{-e}(T)$ determined above in conjunction with equations (22) and (23).

$$\frac{d}{dt}[E.SP] = k_e[E][SP] - k_{-e}[E.SP] - \frac{k_{cat}}{K_N}[N][E.SP] \tag{22}$$

where [N] is the nucleotide concentration.

$$\frac{d}{dt}[E.D_i] = k_e[E][D_i] - k_{-e}[E.D_i] + \frac{k_{cat}}{K_N}[N]\{[E.D_{i-1}] - [E.D_i]\} \tag{23}$$

wherein [E.SP] is concentration of enzyme bound hybridized DNA strand concentration and [N] is the nucleotide concentration. In view of the foregoing derivation and analysis, the following non-limiting examples are provided.

Example 1

Determination of Annealing Temperature (1$^{st}$ PCR Cycle)

Input Data:

Denaturation temperature is 95° C., denaturation time is 30 sec. Extension temperature is 72° C. Annealing and extension times are both 30 sec. The set of possible annealing temperatures is provided in the FIG. 13. We can set any predetermined threshold DNA concentration value and for the specified annealing time (30 sec), find the annealing temperature at which the curve crosses this threshold graphically—this sets annealing temperature. The sequences of the primers are P1=5' GCTAGCTGTAACTG 3'; P2-5' GTCTGCTGAAACTG 3'. S1 and S2 are 500 bp sequences with terminal primer binding sites fully complementary to the sequences above. Primer, enzyme and dNTP concentrations are 0.2 µM, 2 nM and 800 µM respectively. Consistent with the rate equations described hereinabove, a detailed set of rate equations employed in this example are as follows:

Melting $$\frac{d}{dt}[DNA] = k_{-m}[S_1][S_2] - k_m[DNA]$$

Annealing $$\frac{d}{dt}[S_jP_j] = k_f^j[S_j][P_j] - k_r^j[S_jP_j] - k_e[E][S_jP_j] + k_{-e}[E.S_jP_j], \; j = 1, 2$$

$$\frac{d}{dt}[P_j] = -k_f^j[S_j][P_j] + k_r^1[S_jP_j], \; j = 1, 2$$

$$\frac{d}{dt}[S_j] = k_f^1[S_j][P_j] - k_r^j[S_jP_j] - k_f^*[S_1][S_2] + k_r^*[S_1S_2], \; j = 1, 2$$

Employing the analytical steps set forth in Sections I and II(A) hereinabove, $k_f$ and $k_r$ for each primer are determined for the annealing reaction at the three annealing temperatures of 30° C., 35° C. and 40° C. provided in FIG. 13. From this, the primer hybridized DNA strand concentration can be determined at any time. Such information can be used in the solution of the system of rate equations governing the entire PCR cycle to select annealing temperature(s) and/or time(s) for enhancing amplification efficiency. For example, a temperature for DNA extension is selected and $k_e$ and $k_{-e}$ are determined employing the analytical steps set forth in Sections I and II(B) hereinabove. Consistent with the rate equations described hereinabove, a detailed set of rate equations for enzyme binding and extension employed in this example are as follows:

Enzyme Binding and Extension $$\frac{d}{dt}[E.S_jP_j] = k_e[E][S_jP_j] - k_{-e}[E.S_jP_j] - k_{cat}\frac{[E.S_jP_j][N]}{K_N}, j = 1, 2$$

$$\frac{d}{dt}[S_jP_j] = k_{-e}[E.S_jP_j] - k_e[S_jP_j][E], j = 1, 2$$

$$\frac{d}{dt}[E.D_i^j] = \frac{k_{cat}}{K_N}[N]\{[E.D_{i-1}^j] - [E.D_i^j]\} - k_{-e}[E.D_i^j] + k_e[D_i^j][E],$$

$$i = 1, \ldots, n-1; j = 1, 2$$

$$\frac{d}{dt}[D_i^j] = k_{-e}[E.D_i^j] - k_e[D_i^j][E], i = 1, \ldots, n-1; j = 1, 2$$

$$\frac{d}{dt}[E.D_n^j] = \frac{k_{cat}}{K_N}[N][E.D_{n-1}^j] - k'_{cat}[E.D_n^j], j = 1, 2$$

$$\frac{d}{dt}[DNA] = k'_{cat}\{[E.D_n^1] + [E.D_n^2]\}$$

$$\frac{d}{dt}[N] = -\frac{k_{cat}}{K_N}[N]\left\{[E.S_1P_1] + [E.S_2P_2] + \sum_{i=1_l}^{n-1}([E.D_i^1] + [E.D_i^2])\right\}$$

From this, the DNA concentration can be determined at any reaction time. Combining the solved rate equations of annealing at the three different temperatures with the solved extension kinetics provides solutions to the system of rate equations governing the entire PCR cycle to select annealing temperature(s) and/or time(s) for enhancing amplification efficiency. Alternatively the complete set of rate constants can be calculate at both the annealing and extension temperatures using the analytical methods in Sections I and II and the complete set of rate equations above can be solved simultaneously for both annealing and extension steps. FIG. 14 illustrates solutions to the system of rate equations for the entire PCR cycle for the three different annealing temperatures for the primer set. From FIG. 14, it can be seen that annealing temperatures of 30° C. and 35° C. provide greater concentrations of final DNA product than an annealing temperature of 40° C. It can also been seen from FIG. 14 that a desired threshold of DNA concentration can be preselected and the PCR cycle run at a temperature and for a time period for achieving the selected DNA threshold.

Example 2

Calculation of Extension Time (Multiple PCR Cycles)

Input Data:
The thermostable DNA polymerase is Taq polymerase. The primers are the same as those used in Example 1. The set of possible extension times is 30 seconds to 120 seconds in intervals of 0.1 second. The method for optimal extension time determination for three different PCR denaturation/annealing protocols is illustrated: a) 30 s denaturation time at 95 C; 30 s annealing time at 35 C; b) 30 s denaturation time at 95 C; 30 s annealing time at 40 C; c) 30 s denaturation time at 95 C; 120 s annealing time at 35 C. For the purposes of this example the predetermined extension temperature is set to 72° C. The threshold DNA concentration is 100 nM. The sequences of the primers are the same as in Example 1, template length is 500 bp. Species concentrations are the same as in Example 1.

Annealing rate constants for primer hybridized DNA strand concentration are determined as set forth in Example 1 and/or Sections I and II(A) hereinabove. Similarly, extension rate constants are determined as set forth in Example 1 and/or Sections I and II(B) hereinabove. With these rate constants determined, the optimal extension time is determined as follows.

Let $0 \le \eta \le 1$ be the efficiency in the first PCR cycle and the $n(\eta)$ be the number of cycles in stage 1, then $$(1 + \eta)^n = y \tag{24}$$

where $$y = \frac{[DNA]_n}{[DNA]_o}$$

and $[DNA]_n$ is the concentration of DNA after n cycles and $[DNA]_o$ is the initial concentration of DNA. From equation (30), the number of cycles $n(\eta)$ can be expressed as follows:

$$n(\eta) = \frac{\log(y)}{\log(1 + \eta)} \tag{25}$$

Let $t(\eta)$ be the time required for a cycle to achieve an efficiency of $\eta$ and the overall reaction time for state 1 be $t_{total}(\eta)$; (then $$t_{total}(\eta) = n(\eta)t(\eta) = t(\eta)\frac{\log(y)}{\log(1 + \eta)} \tag{26}$$

t(n) is computed by solving the annealing and extension rate equations listed above. Now, the following optimization problem to minimize the overall reaction time $t_{total}$ is considered:

$$\min_\eta t_{total}(\eta) = \min_\eta t(\eta)\frac{\log(y)}{\log(1 + \eta)} \tag{27}$$

Hence, $\eta$ is sought such that $$\frac{d\left(t(\eta)\frac{\log(y)}{\log(1 + \eta)}\right)}{d\eta} = 0 \Rightarrow \frac{1}{t(\eta)}\frac{dt}{d\eta} = \frac{1}{(1 + \eta)(\log(1 + \eta))} \tag{28}$$

The above equation is solved graphically by plotting the left hand side and the right hand side of the above equation with respect to $\eta$. From the given DNA concentration profile, it is possible to estimate the optimal efficiency ($\eta^*$) and hence $t(\eta^*)$ that minimizes the overall reaction time for geometric growth in state 1 subject to the specified constraints.

Table 2 compares the overall reaction time under these three conditions and it can be observed that given this sample set, it is possible to reduce the overall reaction time at the specific reaction temperatures. FIG. 16 compares the geometric growth of DNA with respect to reaction time under the above three reaction conditions. FIG. 17 illustrates the modified temperature protocol based on this analysis. Further, FIG. 18 illustrates optimal cycle efficiency at the three different reaction conditions. The optimal extension times corresponding to the three examples described above are found to be a) 27.8 seconds, b) 24.5 seconds and c) 15.3 seconds.

Example 3

Solution of DAE for Determination of Optimal PCR Annealing/Extension Protocol (Fixed Cycle Time)

The temperature cycling protocol for PCR can be automatically determined by solving an optimal control problem. The optimal control problem, in some embodiments, is of the following form, which maximizes DNA product concentration at a fixed final time:

$$\min_{T(t)} J, J = \sum_{i=1}^{4n+4} x_i(t_f)$$

subject to the constraint $$\frac{dx}{dt} = f(x(t), T(t), k), x(0) = x_0$$

where T(t) denotes the temperature of the reaction mixture as a function of reaction time, $x=[[S_1], [S_1P_1], [E.S_1P_1], [D_1^{\ 1}], [E.D_1^{\ 1}], \ldots, [DNA], [P_1], [P_2], [N], [E]]^{Tr}$ is the vector of concentrations of all reaction species, $x_0$ denotes the vector of initial concentrations, $t_f$ denotes the predetermined time for a single PCR cycle, and f(x(t), T(t), k) denotes the right-hand side of the system of rate equations for primer annealing, enzyme binding and polymerase-mediated extension and k is a vector of all kinetic rate constants appearing in the system of PCR rate equations. f(x(t), T(t), k) can be expressed in terms of the sequence-dependent rate constants $k_i$, appearing in $$\left[k_m, k_{-m}, k_f^1, k_r^1, k_f^2, k_r^2, k_e, k_{-e}, \frac{k_{cat}}{K_N}, k'_{cat}\right] \text{ as } \sum_i k_i(T(t))g_i(x(t))$$

$g_i(x(t))$ denotes the part of the right-hand side of the system of rate equations for DNA melting, primer annealing, enzyme binding and polymerase-mediated extension associated with rate constant $k_i$. The $k_i$ T(t)) are determined according to the analytical methods described hereinabove in Sections I and II. Then, the PCR dynamic model can be expressed as $$\frac{dx(t)}{dt} = \sum_{i=1}^{10} k_i(T(t))g_i(x(t))$$

$$k \in \mathbb{R}^{10}; k \geq 0; x, g_i(x) \in \mathbb{R}^{4n+9}, x \geq 0; h(x) \in \mathbb{R}^5, h(x) = 0$$

$$k = \left[k_m, k_{-m}, k_f^1, k_r^1, k_f^2, k_r^2, k_1^e, k_{-1}^e, \frac{k_{cat}}{K_N}, k'_{cat}\right] \quad (29)$$

where n denotes the number of base pairs, $g_1(x)$ to $g_2(x)$ represent melting alone, $g_3(x)$ to $g_6(x)$ represent the annealing reactions alone and $g_7(x)$ to $g_{10}(x)$ represent the extension reactions and h(x) denotes a set of 5 independent nonlinear constraints enforcing mass balance, which cause the system to evolve on a state manifold $X \subset \mathbb{R}^{4n+9}$ that is of dimension 4n+4. Hence the dimension of the state manifold is also sequence dependent. Additional constraints, including equality constraints may also be applied to the vector of rate constants k. Therefore, the equality and inequality constraints on controls are sequence-dependent. As a result of this, the $k_g$, in equation (29) are also sequence-dependent.

For n=2, $x=[[S_1], [S_1P_1], [E.S_1P_1], [D_1^{\ 1}], [E.D_1^{\ 1}], [E.D_2^{\ 1}], [S_2], [S_2P_2], [E.S_2P_2], [D_1^{\ 2}], [E.D_1^{\ 2}], [E.D_2^{\ 2}], [DNA], [P_1], [P_2], [N], [E]]^{Tr}$. g(x) for a PCR reaction with n=2 is presented in FIG. 19. Additional equality constraints for the state variables are given below.

$$h_1(x) = x_{14}^0 - x_1^0 + x_1 - x_{14} \quad (30)$$

$$h_2(x) = x_{15}^0 - x_7^0 + x_7 - x_{15} \quad (31)$$

$$h_3(x) = x_1^0 + x_7^0 - \left(\sum_{i=1}^{13} x_i\right) - \left(\frac{x_{16}}{K_N}\right)\left(\sum_{i=3,5,9,11} x_i\right) \quad (32)$$

$$h_4(x) = \frac{x_{16}^0 - \left(\sum_{i=4,5,10,11} x_i\right) - 2(x_6 + x_{12} + x_{13})}{\left(1 + \frac{1}{K_N}\right)\left(\sum_{i=5,11} x_i\right)} - x_{16} \quad (33)$$

$$h_5(x) = x_{17}^0 - \left(1 + \frac{x_{16}}{K_N}\right)\left(\sum_{i=3,5,9,11} x_i\right) - x_6 - x_{12} \quad (34)$$

The additional algebraic constraint $T_1 \leq T \leq T_2$ is imposed on the dynamic optimization problem, where $T_1$ and $T_2$ denote predetermined minimum and maximum allowed reaction temperatures (e.g. 30° C. and 95° C.) respectively.

Input Data:

A fixed time PCR optimal control problem with the primer sequences mentioned above and the same reaction conditions (length of target=500 base pairs) has been solved as an example. The reaction time is fixed to be 75 seconds. The denaturation step is not optimized and is set to 95° C./30 s. The lower and upper bounds $T_1$ and $T_2$ on the temperature are set to 30° C. and 95° C., respectively.

The optimization problem is formulated as a system of differential-algebraic equations (DAE) of:

$$H[x(t), \phi(t), T(t)] = \phi^{Tr}(t)\sum_{i=1}^{10} k_i(T(t))g_i(x(t))$$

$$\frac{d\phi}{dt} = -\nabla_x H[x(t), \phi(t), T(t)] = -\sum_{i=1}^{10} k_i(T(t))\left(\frac{\partial g_i(x(t))}{\partial x(t)}\right)^{Tr} \phi(t)$$

$$\phi(t_f) = [\nabla_x F(x(t))]_{t=t_f} = \left[\nabla_x \sum_{i=1}^{4n+4} x_i(t)\right]_{t=t_f}$$

$$\frac{\partial H}{\partial T(t)}[x^*(t), \phi^*(t), T^*(t)] = \phi^{*,Tr}(t)\sum_{i=1}^{10} \frac{\partial k_i(T(t))}{\partial T(t)}\bigg|_{T^*(t)} g_i(x^*(t)) = 0, \quad (35)$$

$$\forall t \in [0, t_f]$$

H[x(t), φ(t), T(t)] is the PMP-Hamiltonian function. φ represents the co-state (a function of time similar to a Lagrange multiplier and analogous to momentum in Hamiltonian mechanics).

FIG. 20 illustrates a flow chart for the Control Vector Iteration (CVI) method that was used to solve the optimal control problem. With reference to FIG. 20, the following steps are provided.

1. For a given initial trajectory of $T_0(t)$ and initial condition $x_0$, the state equations are integrated from $t_0$ to $t_f$ and $x(t)$ is obtained.
2. Boundary condition for the co-state vector is obtained using equation:

$$\frac{\partial H}{\partial T(t)}[x^*(t), \phi^*(t), T^*(t)] = \phi^{*,Tr}(t) \sum_{i=1}^{10} \frac{\partial k_{i,seq}(T(t))}{\partial T(t)}\bigg|_{T^*(t)} g_i(x^*(t)) = 0, \quad (36)$$

$$\forall\, t \in [0, t_f]$$

3. Co-state equations are integrated backwards from $t_f$ to $t_0$ and $\varphi(t)$
4. Using $x(t)$, $\varphi(t)$, and $T_0(t)$, at each t, $$\frac{\partial H}{\partial T(t)}$$

was found.
5. Using $x(t_f)$, the objective function value J was found.
6. If $J \leq J_{desired}$ and $$\left\|\frac{\partial H}{\partial T(t)}\right\| \leq \epsilon,$$

the iterative process was stopped at this point, otherwise the iteration was continued until the next step.
7. Golden section line search method was followed to estimate the optimal $\alpha(t)$.
With the available state and co-state variables, the manipulated variable is updated based on the steepest descent methods such that the nominal control profile satisfies equation (36). The following equation describes the steepest descent method.

$$T_{i+1}(t) = T_i(t) - \alpha \frac{\partial H}{\partial T(t)} \quad (37)$$

Where $\alpha$ is a steepest descent parameter which is generally assumed to be a constant in a conventional CVI. In order to accelerate the process, $\alpha$ can be estimated through line search via the following minimization.

$$\min_{\alpha} F(\alpha(t)) = H\left[x(t), \phi(t), T(t) - \alpha \frac{dH}{dt}(t)\right] \quad (38)$$

A golden section search algorithm is employed for the above minimization.
8. The control profile is updated as per equation (37).
9. With the updated control profile, step 1 is reinitiated and other steps are followed until the iteration satisfies the convergence criteria, $J \leq 0.05$ and $$\left\|\frac{\partial H}{\partial T(t)}\right\| \leq 10^{-4}$$

FIGS. 21 and 22 show the optimal annealing and extension temperature profile and the corresponding optimal DNA concentration profile by solving the PCR optimal control problem by CVI. The efficiency at the optimal operating condition is 96%. The optimal control solutions T(t) for stage 1 are periodic. Hence the T(t) from FIG. 22 can be applied repeatedly for the first 14 PCR cycles. These are optimal PCR cycling strategies for fixed cycle time. FIG. 23 depicts the convergence of the algorithm.

Alternatively, the optimal control problem, in some embodiments, is of the form:

$$\min_{T(t)} J, \quad J = t_f$$

subject to the constraints $$\frac{dx}{dt} = f(x(t), T(t), k),\ x(0) = x_0 \qquad \text{iii)}$$

$$[DNA](t_f) = [DNA]_{target} \qquad \text{ii)}$$

where T(t) denotes the temperature of the reaction mixture as a function of reaction time, is the vector of concentrations of all reaction species, $t_f$ denotes the predetermined time for a single PCR cycle, and f(x(t), T(t), k) denotes the right-hand side of the system of rate equations for primer annealing, enzyme binding and polymerase-mediated extension and k is a vector of all kinetic rate constants appearing in the system of rate equations. As described above, f(x(t), T(t), k) can be expressed in terms of the sequence-dependent rate constants $k_i$ appearing in $$\left[k_m, k_{-m}, k_f^1, k_r^1, k_f^2, k_r^2, k_e, k_{-e}, \frac{k_{cat}}{K_N}, k'_{cat}\right] \text{ as } \sum_i k_i(T(t))g_i(x(t))$$

In such embodiments, the optimal control problem is expressed as the DAE of:

$$H[x(t), T(t), \phi(t)] = L[x(t), T(t)] + \phi^{Tr}(t)\sum_{i=1}^{10} k_i(T(t))g_i(x(t)) = \quad (39)$$

$$1 + \phi^{Tr}(t)\sum_{i=1}^{10} k_i(T(t))g_i(x(t))$$

$$\frac{d\phi}{dt} = -\nabla_x H = -\sum_{i=1}^{10} k_i(T(t))\left(\frac{\partial g_i(x(t))}{\partial x(t)}\right)^{Tr}\phi(t)$$

$$\frac{\partial H}{\partial T(t)}[x^*(t), \phi^*(t), T^*(t)] = \phi^{*,Tr}(t)\sum_{i=1}^{10} \frac{\partial k_i(T(t))}{\partial T(t)}\bigg|_{T^*(t)} g_i(x^*(t)) = 0,$$

$$\forall\, t \in [0, t_f]$$

$$\phi_i(t_f) = 0,\ i = 1, \ldots, 4n+4$$

$$x_{4n+5}(t_f) = x_{4n+5,f},\ x_{4n+5,f} > 2^m x_{4n+5}(0).$$

$$H|_{t_f} = 0 \Longrightarrow \phi^{Tr}(t_f)\sum_{i=1}^{10} k_i(T(t_f))g_i(x(t_f)) = -1$$

where $x_{4n+5,f} = [DNA]_f$ and m denotes the number of cycles for which the time optimal solution is required. Thus, if m=1, $x_{4n+5,f} \geq 2x_{4n+5}$ (0), which implies that more than one cycle will be generated; the single cycle time optimal temperature profile is obtained by considering T(t) up to the switching time between cycles. Equations (35) and (39) can be solved using any differential-algebraic equation solver.

Various embodiments of the invention have been described in fulfillment of the various objects of the invention. It should be recognized that these embodiments are merely illustrative of the principles of the present invention. Numerous modifications and adaptations thereof will be readily apparent to those skilled in the art without departing from the spirit and scope of the invention.

$$\frac{k_f}{k_r} = [C_o]\exp\left(\frac{-\Delta G}{RT}\right) \quad (1)$$

wherein $[C_0]$ is the standard concentration, R is the gas constant and T is the annealing reaction temperature.

The invention claimed is:

1. A computer implemented method for enhancing annealing efficiency of first and second single strands of a sequence of deoxyribonucleic acid (DNA) over a predetermined time period, the method comprising:
   receive information comprising sequences of the first and second DNA strands, concentrations of the first and second DNA strands, length of the predetermined time period and a set of annealing reaction temperatures;
   determine the forward reaction rate constant, $k_f$, of annealing the first and second single strands of DNA at annealing reaction temperatures in the set;
   determine the reverse reaction rate reaction rate constant, $k_r$, of annealing the first and second single strands of DNA at annealing reaction temperatures in the set;
   select one or more of the annealing reaction temperatures based on values determined for the $k_f$ and $k_r$ sufficient for amplification of the sequence of DNA to a concentration from the annealed first and second strands in excess of a predetermined threshold within the predetermined time period; and
   amplifying the sequence of DNA to the concentration in excess of the predetermined threshold within the predetermined time period according to the selected one or more annealing reaction temperatures.

2. The computer implemented method of claim 1, wherein $k_f$ and $k_r$ are determined according to Gibbs free energy ($\Delta G$) for the annealing reaction and relaxation time for the annealing reaction.

3. The computer implemented method of claim 2, wherein $k_f/k_r$ is expressed in terms of the Gibbs free energy through equation 1 as:

4. The computer implemented method of claim 3, wherein the relaxation time is expressed in equation 2 as:

$$\tau = 1/(k_f[S_{2eq}+S_{1eq}]+k_r) \quad (2)$$

wherein $S_{1eq}$ and $S_{2eq}$ are equilibrium concentrations of the first and second DNA single strands.

5. The computer implemented method of claim 4, wherein values of $k_f$ and $k_r$ are obtained from equations 1 and 2 for a given value of tau.

6. The computer implemented method of claim 5, wherein the given value of $\tau$ is determined according to $\tau = -1/\lambda_{max}$, wherein $\lambda_{max}$ denotes the largest eigenvalue of an annealing reaction matrix:

$$A = \begin{bmatrix} -(k^{-1}+k_{-1}) & k_1 & k_1 & 0 \\ k_{-1} & -(k_{-2}+k_1) & 0 & \sigma[D_{0,2eq}]k_1 \\ k^{-1} & 0 & -(k^{-2}+k_1) & \sigma[D_{0,2eq}]k_1 \\ 0 & k_{-2} & k^{-2} & -2\sigma[D_{0,2eq}]k_1 \end{bmatrix}$$

wherein $k_0 = k_1 = k_2$ which equal the forward rate constant for formation of a single base pair and $k_{-i}$ is the reverse rate constant for the formation of the single base pair wherein $k_{-i} = s_i/k_0$ where s is the equilibrium constant for formation of base pair i, and $\sigma$ is a nucleation parameter that measures resistance to formation of the first base pair and wherein $D_{0,2eq}$ is the number of base pairs melted from left and right sides of the DNA.

7. The computer implemented method of claim 1, wherein the DNA concentration, [D], is determined according to:

$$d[D]/dt = k_f[S_1][S_2] - k_r[D]$$

wherein [S$_1$] is concentration of the first DNA single strand and [S$_2$] is concentration of the second DNA single strand.

8. A computer implemented method for enhancing annealing efficiency of first and second single strands a sequence of deoxyribonucleic acid (DNA) at a predetermined temperature, the method comprising:
  receive information comprising sequences of the first and second DNA strands, concentrations of the first and second DNA strands, the predetermined annealing reaction temperature and a set of annealing reaction time periods;
  determine the forward reaction rate constant, k$_f$, of annealing the first and second single strands of DNA;
  determine the reverse reaction rate reaction rate constant, k$_r$, of annealing the first and second single strands of DNA;
  select one or more of the annealing reaction time periods based on values determined for the k$_f$ and k$_r$ sufficient for amplification of the sequence of DNA to a concentration from the annealed first and second strands in excess of a predetermined threshold at the predetermined annealing reaction temperature; and
  amplifying the sequence of DNA to the concentration in excess of the predetermined threshold at the predetermined annealing reaction temperature according to the selected one or more annealing reaction time periods.

9. The computer implemented method of claim 8, wherein the DNA concentration, [D], is determined according to:

$$d[D]/dt = k_f[S_1][S_2] - k_r[D].$$

10. A computer implemented method for enhancing amplification efficiency of a sequence of deoxyribonucleic acid (DNA) in a first cycle of polymerase chain reaction (PCR), the method comprising:
  (a) receive information comprising sequences of single strand DNA and primer, concentrations of the single strand DNA and primer, length of a predetermined time period for annealing the single strand DNA and primer and a set of annealing reaction temperatures;
  (b) determine the forward reaction rate constant, k$_f$, of annealing the single strand DNA and primer at annealing reaction temperatures in the set;
  (c) determine the reverse reaction rate reaction rate constant, k$_r$, of annealing the single strand DNA and primer at reaction temperatures in the set;
  (d) select one or more of the annealing reaction temperatures based on values determined for the k$_f$ and k$_r$ sufficient for amplification of a primer hybridized DNA strand concentration in excess of a predetermined threshold within the predetermined time period for annealing; and
  (e) amplifying the hybridized DNA strand concentration in excess of the predetermined threshold within the predetermined time period for annealing according to the selected one or more annealing reaction temperatures.

11. The computer implemented method of claim 10, wherein k$_f$ and k$_r$ are determined according to Gibbs free energy for the annealing reaction and relaxation time for the annealing reaction.

12. The computer implemented method of claim 11 wherein relationship between the Gibbs free energy, k$_f$ and k$_r$ is expressed as:

$$\frac{k_f}{k_r} = [C_o]\exp\left(\frac{-\Delta G}{RT}\right)$$

wherein [C$_0$] is the standard concentration, R is the gas constant and T is the annealing reaction temperature.

13. The computer implemented method of claim 11, wherein the relaxation time is expressed as:

$$\tau = 1(k_f[P_{eq} + S_{eq}] + k_r)$$

wherein P$_{eq}$ and S$_{eq}$ are equilibrium concentrations of the primer and single strand DNA.

14. The computer implemented method of claim 10, wherein the hybridized DNA strand concentration, [SP], is determined according to:

$$d[SP]/dt = k_f[S][P] - k_r[SP]$$

wherein [P] is concentration of the primer and [S] is concentration of the single strand DNA.

15. The computer implemented method of claim 10, wherein the computing device processor further (f) determines a temperature for DNA extension sufficient to produce a concentration of DNA in excess of a predetermined threshold within a predetermined extension time period.

16. The computer implemented method of claim 10, wherein the computing device processor further (f) determines a time period for DNA extension sufficient to produce a concentration of DNA in excess of a predetermined threshold.

17. The computer implemented method of claim 10, wherein the time period for DNA extension is determined at a predetermined temperature of DNA extension.

18. The computer implemented method of claim 17, wherein determining the time period for DNA extension comprises determining the forward reaction rate constant, k$_e$, of DNA polymerase binding and determining the reverse reaction rate constant, k$_{-e}$, of DNA polymerase binding.

19. The computer implemented method of claim 18, wherein k$_e$ and k$_{-e}$ are determined according to the Gibbs free energy for the DNA polymerase binding reaction and processivity of the polymerase through the relationship:

$$k_{-e} = \frac{k_{cat}}{K_N}[N]\left(\frac{1}{E[i_{off}] - 1}\right)$$

where [N] is the nucleotide concentration and i indexes the sequence position on the template, $$\frac{k_{cat}}{K_N}$$

is the catalytic rate constant of nucleotide addition, and $$E[i_{off}] = \frac{1}{1-p}$$

is the processivity or expected position of dissociation of the polymerase, with p denoting the microscopic processivity parameter, the microscopic processivity parameter being the conditional probability of the polymerase not dissociating at position/time i, given that it was bound to the template at position i−1.

20. The computer implemented method of claim 18, wherein determining the time period for DNA extension further comprises determining the enzyme bound primer-template DNA strand concentration, [E.SP], according to:

$$\frac{d}{dt}[E.SP] = k_e[E][SP] - k_{-e}[E.SP] - \frac{k_{cat}}{K_N}[N][E.SP]$$

wherein [N] is nucleotide concentration.

21. The computer implemented method of claim 20, wherein determining the time period for DNA extension further comprises determining the concentration of enzyme bound primer-template DNA with i added nucleotides, [E.D$_i$], according to:

$$\frac{d}{dt}[E.D_i] = k_e[E][D_i] - k_{-e}[E.D_i] + \frac{k_{cat}}{K_N}[N]\{[E.D_{i-1}] - [E.D_i]\}$$

where [N] is the nucleotide concentration and [D$_i$] is the concentration of primer-template DNA with i added nucleotides.

22. The method of claim 21, wherein $K_N$ and $k_{cat}$ are experimentally or theoretically determined, wherein $K_N$ is the Michaelis constant for nucleotide binding to the enzyme-primer-template DNA strand and $k_{cat}$ is the catalytic rate constant of nucleotide addition to the enzyme-primer-template DNA strand.

23. The computer implemented method of claim 21, wherein $K_N$ and $k_{cat}$ are determined from a plot of 1/v versus 1/[N] wherein the slope of the plot is $$\frac{K_N}{k_{cat}E_0}$$

and the y-intercept is $$\frac{1}{k_{cat}E_0},$$

wherein $E_0$ is the initial concentration of DNA polymerase and v is an experimentally or theoretically determined rate of reaction for nucleotide addition.

24. The computer implemented method of claim 10 wherein the computing device processor further (a') determines a time period for duplex DNA melting sufficient to produce a concentration of single strand DNA in excess of a predetermined threshold.

25. The method of claim 24, wherein determining the time period for duplex DNA melting comprising determining forward and reverse rate constants of duplex DNA melting by at least one of:
   (1) identification of different melting domains for a given DNA sequence using an algorithmic method;
   (2) computing the equilibrium constant and melting temperature of each domain via the equation:

$$K_{eq,dom} = \sigma_c f(N) \prod_{i=1}^{N} s_i$$

where N is the domain length, $s_i$ is the equilibrium constant for formation of base pair i and $\sigma_c$ is the cooperativity parameter that constitutes a penalty on the statistical weight $$\prod_{i=1}^{N} s_i$$

for melting of the domain due to the free energy cost of dissociation of an internal base pair, and f(N) is a loop closure function specific to the type of domain that introduces a length dependence on the free energy cost;
   (3) construction of state space matrix blocks as in claim 6 based on a two-sided or one sided matrix for each domain;
   (4) association of σ, the nucleation parameter with individual states in a last block as in claim 6;
   (5) diagonalization of each block and rank ordering of eigenvalues of all blocks;
   (6) determining relaxation time, τ, according to 1/max ($\lambda_i$), wherein max($\lambda_i$) denotes the largest eigenvalue of an annealing reaction matrix $$A = \begin{bmatrix} -\sigma[D_{0eq}]k_1 & k_{-0} & 0 & 0 & \cdots \\ \sigma[D_{0eq}]k_1 & -k_1-k_{-0} & k_{-1} & 0 & \cdots \\ 0 & k_1 & -k_1-k_{-1} & k_{-2} & \cdots \\ 0 & 0 & k_1 & -k_{-2} & \cdots \\ \vdots & \vdots & \vdots & \vdots & \ddots \end{bmatrix}$$

wherein $k_0=k_1=k_2$ which equal the forward rate constant for formation of a single base pair and $k_{-i}$ is the reverse rate constant for the formation of the single base pair wherein $k_{-1}=s_i/k_0$ where s is the equilibrium constant for formation of base pair i, and σ is a nucleation parameter that measures resistance to formation of the first base pair;
   (7) comparing all relations times, τ, and identifying the maximum value of the relaxation time as relaxation time of the whole DNA sequence; and
   (8) computing forward and reverse rate constants ($k_m$, $k_{-m}$, respectively) for DNA melting based on the relaxation time, \tau, and the Gibbs free energy of melting as expressed in claim 5.

26. The computer implemented method of claim 16, wherein the instructions cause the computing device processor to repeat steps (a)-(f) for enhancing amplification efficiency of the sequence of DNA in at least one additional cycle of PCR.

27. The computer-implemented method of claim 23, wherein amplification of the DNA concentration in excess of the predetermined threshold is achieved through an algorithm that solves an optimization problem of the form $$\min_{T(t)} J, J = \sum_{i=1}^{4n+4} x_i(t_f)$$

subject to the constraint $$\frac{dx}{dt} = f(x(t), T(t), k), x(0) = x_0$$

where T(t) denotes reaction mixture temperature as a function of reaction time, $x=[[S_1], [S_1P_1], [E.S_1P_1], [D_1^1], [E.D_1^1], \ldots, [DNA], [P_1], [P_2], [N], [E]]^{Tr}$ is the vector of concentrations of all reaction species listed in the vector, $x_0$ denotes the vector of initial concentrations, $t_f$ denotes predetermined time for a single PCR cycle, and f(x(t), T(t), k) denotes the right-hand side of the system of rate equations for primer annealing, enzyme binding and polymerase-mediated extension and k is a vector of all kinetic rate constants appearing in the system of PCR rate equations.

28. The computer-implemented method of claim 27, wherein f(x(t), T(t), k) is expressed in terms of the sequence-dependent rate constants $k_i$ appearing in $$\left[k_m, k_{-m}, k_f^1, k_r^1, k_f^2, k_r^2, k_1^e, k_{-1}^e, \frac{k_{cat}}{K_N}, k'_{cat}\right] \text{ as } \sum_i k_i(T(t))g_i(x(t))$$

g(x(t)) denotes the part of the right-hand side of the system of rate equations for DNA melting, primer annealing, enzyme binding and polymerase-mediated extension associated with rate constant $k_i$.

29. The computer-implemented method of 27, where the additional algebraic constraint $$T_{min} \leq T \leq T_{max},$$

is imposed in the dynamic optimization problem, where $T_{min}$ and $T_{max}$ denote predetermined minimum and maximum allowed reaction temperatures, respectively.

30. The computer-implemented method of claim 23, wherein amplification of the DNA concentration in excess of the predetermined threshold is achieved through an algorithm that solves an optimization problem of the form:

$$\min_{T(t)} J, J = t_f$$

subject to the constraints $$\frac{dx}{dt} = f(x(t), T(t), k), x(0) = x_0 \quad \text{i)}$$

$$[DNA](t_f) = [DNA]_{target} \quad \text{ii)}$$

where T(t) denotes the temperature of the reaction mixture as a function of reaction time and is the vector of concentrations of all reaction species, $t_f$ denotes the predetermined time for a single PCR cycle, and f(x(t), T(t), k) denotes the right-hand side of the system of rate equations for primer annealing, enzyme binding and polymerase-mediated extension and k is a vector of all kinetic rate constants appearing in the system of rate equations.

31. The computer-implemented method of claim 30, wherein f(x(t), T(t), k) is expressed in terms of the sequence-dependent rate constants $k_i$ appearing in $$\left[k_m, k_{-m}, k_f^1, k_r^1, k_f^2, k_r^2, k_1^e, k_{-1}^e, \frac{k_{cat}}{K_N}, k'_{cat}\right] \text{ as } \sum_i k_i(T(t))g_i(x(t)).$$

32. The computer-implemented method of claim 28, wherein the optimization problem is formulated as a system of differential-algebraic equations (DAE) of:

$$H[x(t), \phi(t), T(t)] = \phi^{Tr}(t) \sum_{i=1}^{10} k_i(T(t)), g_i(x(t))$$

$$\frac{d\phi}{dt} = -\nabla_x H[x(t), \phi(t), T(t)] = -\sum_{i=1}^{10} k_i(T(t))\left(\frac{\partial g_i(x(t))}{\partial x(t)}\right)^{Tr}\phi(t)$$

$$\phi(t_f) = [\nabla_x F(x(t))]_{t=t_f} = \left[\nabla_x \sum_{i=1}^{4n+4} x_i(t)\right]_{t=t_f}$$

$$\frac{\partial H}{\partial T(t)}[x^*(t), \phi^*(t), T^*(t)] = \phi^{*,Tr}(t) \sum_{i=1}^{10} \frac{\partial k_i(T(t))}{\partial T(t)}\bigg|_{T^*(t)} g_i(x^*(t)) = 0,$$

$$\forall t \in [0, t_f]$$

where H denotes the optimal control Hamiltonian function and φ(t) denotes the optimal control costate vector.

33. The computer implemented method of claim 31, wherein the optimization problem is formulated as a system of differential-algebraic equations (DAE) of:

$$H[x(t), T(t), \phi(t)] =$$

$$L\{x(t), T(t)\} + \phi^{Tr}(t) \sum_{i=1}^{10} k_i(T(t))g_i(x(t)) = 1 + \phi^{Tr}(t) \sum_{i=1}^{10} k_i(T(t))g_i(x(t))$$

$$\frac{d\phi}{dt} = -\nabla_x H = -\sum_{i=1}^{10} k_i(T(t))\left(\frac{\partial g_i(x(t))}{\partial x(t)}\right)^{Tr}\phi(t)$$

$$\frac{\partial H}{\partial T(t)}[x^*(t), \phi^*(t), T^*(t)] = \phi^{*,Tr}(t) \sum_{i=1}^{10} \frac{\partial k_i(T(t))}{\partial T(t)}\bigg|_{T^*(t)} g_i(x^*(t)) = 0,$$

$$\forall t \in [0, t_f]$$

$$\phi_i(t_f) = 0, i = 1, \ldots, 4n+4$$

$$x_{4n+5}(t_f) = x_{4n+5,f}, x_{4n+5,f} > 2^m x_{4n+5}(0).$$

$$H|_{t_f} = 0 \Rightarrow \phi^{Tr}(t_f) \sum_{i=1}^{10} k_i(T(t_f))g_i(x(t_f)) = -1$$

where $x_{4n+5,f}=[DNA]_f$ and m denotes the number of cycles for which the time optimal solution is required.

34. The computer-implemented method of claims 32 and 33, wherein the problem of finding the optimal temperature cycling protocol T*(t) is solved using any differential-algebraic equation solver.

35. A computer implemented method for determining the temperature cycling protocol for a PCR reaction that achieves amplification of DNA concentration in excess of a predetermined threshold, the method comprising:
   a) receive information comprising sequences of single strand DNAs and primers, concentrations of the single strand DNAs and primers, the type of polymerase enzyme, the polymerase enzyme concentration, and the nucleotide concentration;
   b) determine the forward reaction rate constant, $k_f(T)$, of annealing each single strand DNA and primer as a function of temperature T;
   c) determine the reverse reaction rate constant, kr(T), of annealing each single strand DNA and primer as a function of temperature T;
   d) determine the rate constant, $k_e(T)$, of polymerase enzyme binding to the hybridized primer-template DNA as a function of temperature T
   e) determine the rate constant, $k_{-e}(T)$, polymerase enzyme dissociation from the hybridized primer-template DNA as a function of temperature T
   f) determine the Michaelis constant, $K_N(T)$, for nucleotide binding to the enzyme-primer-template DNA complex E.SP as a function of temperature T
   g) determine the catalytic rate constant, $k_{cat}(T)$, of nucleotide addition to the enzyme-primer-template DNA complex E.SP as a function of temperature T
   h) determine the forward rate constant, $k_m(T)$, for dsDNA melting for the complete sequence as a function of temperature T i) determine the reverse rate constant, $k_{-m}(T)$, for dsDNA melting for the complete sequence as a function of temperature T j) solve an optimization problem of the form $$\min_{T(t)} J, \quad J = \sum_{i=1}^{4n+4} x_i(t_f)$$

subject to the constraint $$\frac{dx}{dt} = f(x(t), T(t), k), \quad x(0) = x_0$$

where $T(t)$ denotes the temperature of the reaction mixture as a function of reaction time, $x = [[S_1], [S_1P_1], [E.S_1P_1], [D_1^1], [E.D_1^1], \ldots, [DNA], [P_1], [P_2], [N], [E]]^{Tr}$ is the vector of concentrations of all reaction species listed in the vector, $x_0$ denotes the vector of initial concentrations, $t_f$ denotes the predetermined time for a single PCR cycle, and $f(x(t), T(t), k)$ denotes the right-hand side of the system of rate equations for primer annealing, enzyme binding and polymerase-mediated extension and $k$ is a vector of all kinetic rate constants appearing in the system of PCR rate equations; and k) amplifying the DNA concentration in excess of the predetermined threshold according to the temperature cycling protocol for the PCR reaction that is determined.

* * * * *

SEQUENCE LISTING

```
<160> NUMBER OF SEQ ID NOS: 2

<210> SEQ ID NO 1
<211> LENGTH: 14
<212> TYPE: DNA
<213> ORGANISM: Unknown
<220> FEATURE:
<223> OTHER INFORMATION: Primer Sequence

<400> SEQUENCE: 1
gctagctgta actg                                                       14

<210> SEQ ID NO 2
<211> LENGTH: 14
<212> TYPE: DNA
<213> ORGANISM: Unknown
<220> FEATURE:
<223> OTHER INFORMATION: Primer Sequence

<400> SEQUENCE: 2
gtctgctgaa actg                                                       14
```